United States Patent
Nezhat et al.

(10) Patent No.: US 6,514,252 B2
(45) Date of Patent: *Feb. 4, 2003

(54) BIPOLAR SURGICAL INSTRUMENTS HAVING FOCUSED ELECTRICAL FIELDS

(75) Inventors: Camran Nezhat, Woodside, CA (US); Andrew H. Hancock, Fremont, CA (US); Alan Bachman, New Haven, CT (US)

(73) Assignee: Perfect Surgical Techniques, Inc., Palo Alto, CA (US)

( * ) Notice: Subject to any disclaimer, the term of this patent is extended or adjusted under 35 U.S.C. 154(b) by 0 days.

(21) Appl. No.: 09/910,439

(22) Filed: Jul. 19, 2001

(65) Prior Publication Data

US 2002/0013583 A1 Jan. 31, 2002

Related U.S. Application Data

(63) Continuation-in-part of application No. 09/705,054, filed on Nov. 2, 2000, which is a continuation of application No. 09/303,007, filed on Apr. 30, 1999, now Pat. No. 6,162,220, which is a continuation-in-part of application No. 09/071,689, filed on May 1, 1998, now Pat. No. 6,030,384.

(51) Int. Cl.$^7$ ................................................ A61B 18/18
(52) U.S. Cl. .............................. 606/48; 606/51; 606/50
(58) Field of Search ..................... 606/41, 45, 48–52

(56) References Cited

U.S. PATENT DOCUMENTS

| | | |
|---|---|---|
| 3,920,021 A | 11/1975 | Hiltebrandt |
| 4,016,886 A | 4/1977 | Doss et al. |
| 4,041,952 A | 8/1977 | Morrison, Jr. et al. |
| 4,043,342 A | 8/1977 | Morrison, Jr. |
| 4,671,274 A | 6/1987 | Sorochenko |
| 5,098,431 A | 3/1992 | Rydell |
| 5,151,102 A | 9/1992 | Kamiyama et al. |
| 5,207,691 A | 5/1993 | Nardella |
| 5,217,030 A | 6/1993 | Yoon |
| 5,217,460 A | 6/1993 | Knoepfler |
| 5,267,998 A | 12/1993 | Hagen |
| 5,269,780 A | 12/1993 | Roos |
| 5,269,782 A | 12/1993 | Sutter |
| 5,281,216 A | 1/1994 | Klicek |
| 5,282,799 A | 2/1994 | Rydell |
| 5,290,287 A | 3/1994 | Boebel et al. |
| 5,295,990 A | 3/1994 | Levin |
| 5,300,087 A | 4/1994 | Knoepfler |
| 5,324,289 A | 6/1994 | Eggers |
| 5,330,471 A | 7/1994 | Eggers |
| 5,336,229 A | 8/1994 | Noda |
| 5,342,381 A | 8/1994 | Tidemand |
| 5,352,223 A | 10/1994 | McBrayer et al. |

(List continued on next page.)

FOREIGN PATENT DOCUMENTS

| | | |
|---|---|---|
| EP | 0640315 A1 | 3/1995 |
| EP | 0797959 A1 | 10/1997 |
| FR | 598149 | 7/1925 |
| SU | 197711 | 11/1977 |
| WO | WO 94/17741 A1 | 8/1994 |

*Primary Examiner*—Roy D. Gibson
(74) *Attorney, Agent, or Firm*—Townsend and Townsend and Crew LLP

(57) ABSTRACT

A bipolar surgical device comprises a pair of actuable jaws. A first electrode member which optionally includes a line of electrically coupled tissue-penetrating elements is formed on one of the jaws, and a second electrode member which optionally includes a line of electrically coupled tissue-penetrating elements is formed on the same or the other jaw. The electrode members are laterally spaced-apart and arranged in a parallel, usually linear manner so that the lateral distance therebetween remains generally constant. In operation, tissue may be grasped between the jaws so that the electrode members contact and/or the tissue-penetrating elements enter into the tissue. By energizing the electrode members at opposite polarities using a high frequency energy source, tissue between the jaws will be heated, coagulated, and/or necrosed, while heating of tissue outside of the lines will be minimized.

30 Claims, 26 Drawing Sheets

U.S. PATENT DOCUMENTS

| | | |
|---|---|---|
| 5,352,235 A | 10/1994 | Koros et al. |
| 5,356,408 A | 10/1994 | Rydell |
| 5,383,876 A | 1/1995 | Nardella |
| 5,391,166 A | 2/1995 | Eggers |
| 5,395,369 A | 3/1995 | McBrayer et al. |
| 5,396,900 A | 3/1995 | Slater et al. |
| 5,403,312 A | 4/1995 | Yates et al. |
| 5,417,687 A | 5/1995 | Nardella et al. |
| 5,423,814 A | 6/1995 | Zhu et al. |
| 5,441,499 A | 8/1995 | Fritzsch |
| 5,443,463 A | 8/1995 | Stern et al. |
| 5,445,638 A | 8/1995 | Rydell et al. |
| 5,456,684 A | 10/1995 | Schmidt et al. |
| 5,458,598 A | 10/1995 | Feinberg et al. |
| 5,462,546 A | 10/1995 | Rydell |
| 5,482,054 A | 1/1996 | Slater et al. |
| 5,484,435 A | 1/1996 | Fleenor et al. |
| 5,484,436 A | 1/1996 | Eggers et al. |
| 5,496,312 A | 3/1996 | Klicek |
| 5,496,317 A | 3/1996 | Goble et al. |
| 5,514,134 A | 5/1996 | Rydell et al. |
| 5,527,313 A | 6/1996 | Scott et al. |
| 5,531,744 A | 7/1996 | Nardella et al. |
| 5,540,684 A | 7/1996 | Hassler, Jr. |
| 5,540,685 A | 7/1996 | Parins et al. |
| 5,542,945 A | 8/1996 | Fritzsch |
| 5,549,606 A | 8/1996 | McBrayer et al. |
| 5,558,100 A | 9/1996 | Cox |
| 5,558,671 A | 9/1996 | Yates |
| 5,569,243 A | 10/1996 | Kortenbach et al. |
| 5,573,535 A | 11/1996 | Koros et al. |
| 5,578,052 A | 11/1996 | Viklund |
| 5,582,611 A | 12/1996 | Tsuruta et al. |
| 5,599,350 A | 2/1997 | Schulze et al. |
| 5,603,711 A | 2/1997 | Parins et al. |
| 5,624,452 A | 4/1997 | Yates |
| 5,626,578 A | 5/1997 | Tihon |
| 5,637,110 A | 6/1997 | Pennybacker et al. |
| 5,637,111 A | 6/1997 | Sutcu et al. |
| 5,658,281 A | 8/1997 | Heard |
| 5,662,680 A | 9/1997 | Desai |
| 5,665,085 A | 9/1997 | Nardella |
| 5,665,100 A | 9/1997 | Yoon |
| 5,667,526 A | 9/1997 | Levin |
| 5,669,907 A | 9/1997 | Platt, Jr. et al. |
| 5,674,184 A | 10/1997 | Hassler, Jr. |
| 5,674,220 A | 10/1997 | Fox et al. |
| 5,681,282 A | 10/1997 | Eggers et al. |
| 5,683,385 A | 11/1997 | Kortenbach et al. |
| 5,683,388 A | 11/1997 | Slater |
| 5,688,270 A | 11/1997 | Yates et al. |
| 5,693,051 A | 12/1997 | Schulze et al. |
| 5,697,949 A | 12/1997 | Giurtino et al. |
| 5,700,261 A | 12/1997 | Brinkerhoff |
| 5,702,390 A | 12/1997 | Austin et al. |
| 5,707,369 A | 1/1998 | Vaitekunas et al. |
| 5,709,224 A | 1/1998 | Behl et al. |
| 5,709,680 A | 1/1998 | Yates et al. |
| 5,713,896 A | 2/1998 | Nardella |
| 5,718,703 A | 2/1998 | Chin |
| 5,733,283 A | 3/1998 | Malis et al. |
| 5,735,848 A | 4/1998 | Yates et al. |
| 5,735,849 A | 4/1998 | Baden et al. |
| 5,741,285 A | 4/1998 | McBrayer et al. |
| 5,743,906 A | 4/1998 | Parins et al. |
| 5,755,717 A | 5/1998 | Yates et al. |
| 5,797,941 A | 8/1998 | Schulze et al. |
| 5,833,690 A | 11/1998 | Yates et al. |
| 5,891,142 A | 4/1999 | Eggers et al. |
| 6,030,384 A | 2/2000 | Nezhat |
| 6,162,220 A | 12/2000 | Nezhat |

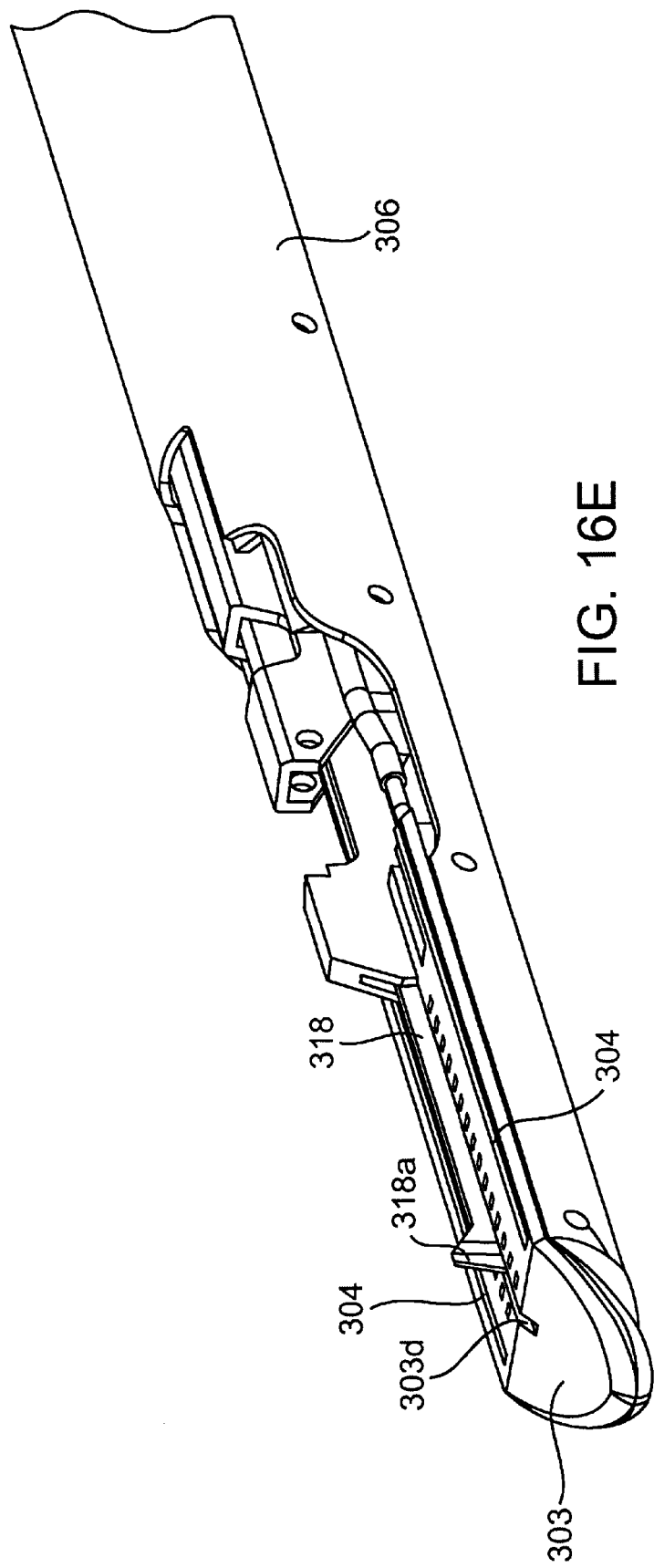

BIPOLAR SURGICAL INSTRUMENTS HAVING FOCUSED ELECTRICAL FIELDS

This application is a continuation-in-part of and claims the benefit of priority from U.S. patent application Ser. No. 09/705,054 filed on Nov. 2, 2000, which is a continuation of U.S. patent application Ser. No. 09/303,007, filed on Apr. 30, 1999, now U.S. Pat. No. 6,162,220, which is a continuation-in-part of U.S. patent application Ser. No. 09/071,689, filed on May 1, 1998, now U.S. Pat. No. 6,030,384, the full disclosures of which are incorporated herein by reference.

BACKGROUND OF THE INVENTION

1. Field of the Invention

The present invention relates generally to medical devices and methods. More particularly, the present invention relates to the structure and use of bipolar forceps and other instruments for coagulating, cutting, and necrosing tissue.

Electrosurgery refers broadly to a class of medical procedures which rely on the application of high frequency electrical energy, usually radiofrequency energy, to patient tissue to achieve a number of possible effects, such as cutting, coagulation, hyperthermia, necrosis, and the like. Of particular interest to the present invention, bipolar electrosurgical devices rely on contacting electrodes of different polarity in close proximity to each other against or into tissue. For example, bipolar forceps 100 (FIGS. 1 and 2) have been used for cutting and coagulating tissue, where the opposed jaws 102 and 104 of the forceps are connected to different poles of an electrosurgical power supply. The high frequency electrical current thus flows from one jaw to the other through the tissue present therebetween. Use of such bipolar forceps is effective for a number of purposes and advantageous in that its effect is generally limited to the tissue held between the jaws. Heating, however, is not totally limited to such intermediate tissue, and in some instances heating of adjacent tissues can be problematic. Such heating occurs because the current flows not only between the jaws but also laterally outward, as shown by flux lines F in FIG. 1B.

Various improvements to bipolar forceps have been proposed. For example, the placement of pins or other tissue-penetrating elements onto the tissue-engaging surface(s) of either or both jaws has been suggested for a variety of purposes. Regardless of the intended purpose, the placement of tissue-penetrating elements on the jaw(s) can marginally focus the current density and somewhat lessen heating of adjacent tissues. Such prior designs employing tissue-penetrating elements, however, still cause unwanted heating of adjacent tissues in at least certain circumstances.

A second problem with conventional bipolar forceps is limited power delivery. With conventional forceps, jaws having a length of about 20 mm and a width of about 5 mm can usually deliver only 25 W of power without causing charring of the tissue. Charring greatly increases electrical resistance through the tissue and can result in premature termination of the treatment. With such a low power level, the time to fully coagulate the tissue can be excessive.

It would therefore be desirable to provide still further improved bipolar forceps and other electrosurgical device designs. In particular, it would be desirable to provide bipolar forceps which provide a very high degree of focused heating, i.e., provide heating of tissue between the jaws with minimized heating of tissue adjacent to the jaws. It would be further desirable to provide bipolar forceps which can deliver higher current flows and densities to the tissue being treated without charring the tissue and terminating the current flow. Such device designs should be relatively simple and easy to fabricate. The devices and methods should be compatible with conventional electrosurgical power supplies and usable in a wide variety of procedures, including cutting, coagulation, and necrosis, where the localized and specific heating of patient tissues is desired. At least some of these objectives will be met by the invention described hereinafter.

2. Description of the Background Art

Radio frequency power apparatus and methods for delivering radio frequency energy to tissue via bipolar surgical instruments are described in co-pending application Ser. No. 09/808,096 filed Mar. 13, 2001, assigned to the assignee of the present application. Bipolar forceps having penetrating elements on opposed jaws thereof are described in U.S. Pat. Nos. 5,527,313 and 5,217,460; Soviet Union Patent Publication SU 197711; and French Patent No. 598,149. Bipolar electrosurgical instruments having laterally spaced-apart electrodes on opposed jaws are described in U.S. Pat. Nos. 5,833,690; 5,702,390; 5,688,270; and 5,403,312. A blood vessel coagulation device having electrode arrays on opposed jaws of forceps is described in U.S. Pat. No. 5,151,102. Other bipolar electrosurgical devices are described in U.S. Pat. Nos. 5,797,941; 5,665,085; 5,662,680; 5,582,611; 5,445,638; 5,441,499; 5,383,876; 5,403,312; 5,098,431; and 4,043,342. A radiofrequency tumor heating device comprising parallel electrode arrays of opposite polarity is described in U.S. Pat. No. 4,016,886.

The full disclosures of each of the above references are incorporated herein by reference.

SUMMARY OF THE INVENTION

The present invention provides improved bipolar surgical instruments, such as forceps, graspers, or the like, which comprise a pair of opposed jaws at the distal end of a shaft. The present devices may be usable in a wide variety of procedures, including open surgical and laparoscopic surgical procedures, and are designed for one-handed operation by a user. The present invention is directed at a unique electrode configuration on either or both of the jaws which will provide improved current focussing characteristics and lessened heating of adjacent tissues. In particular, electrode members on either or both of the jaws will be laterally spaced apart from each other when the jaws are closed so that current will flow from one electrode to the other with minimum current flow outside of the region defined between the electrodes. Optionally, a pair of electrodes can be provided on each jaw with a positive and negative electrode on one jaw and a positive and negative electrode on the other jaw, with the two positive electrodes and the two negative electrodes being aligned with each other when the jaws are closed to define the desired focussed current flow.

At least one of the electrode members will include tissue-penetrating elements. Usually a first line of electrically coupled tissue-penetrating elements will be provided on a first electrode member, and a second line of electrically coupled tissue-penetrating elements will be provided on a second electrode member. Third and fourth lines of electrically coupled tissue-penetrating elements will preferably be provided when third and fourth electrode members are provided on the instrument. The first and second lines (and optionally third and fourth lines) of tissue-penetrating elements will be electrically isolated from each other to permit energization in a bipolar manner, i.e., each line of electrically coupled tissue-penetrating elements may be separately connected to the opposite pole of a conventional electrosurgical power supply. An exemplary radio frequency electrosurgical generator for use with the present invention is described in co-pending application Ser. No. 09/808,096, assigned to the assignee herein. The shaft includes or comprises an actuating mechanism for moving the jaws between opened and closed configurations, where the lines of tissue-penetrating elements lie parallel to and spaced-apart from each other when the jaws are closed. In this way, the jaws can be closed on a target tissue structure, such as a fallopian tube, artery, vein, other hollow organs, and the like, in order to penetrate the lines of elements into the tissue. By then applying high frequency electrical energy to the lines in a bipolar manner, current flux will be focused to within that portion of the tissue which lies between the adjacent lines, with minimum heating of tissue outside of the parallel lines. Usually, but not necessarily, the lines will both be straight. Alternatively, the lines could be nonlinear, e.g., curved, serpentine, zig-zag, or the like, so long as the patterns are similar and the lateral spacing between adjacent points on the lines remains substantially constant. Preferably, the spacing between the adjacent lines of tissue-penetrating elements will be in the range from 0.5 mm to 10 mm, more preferably from 2 mm to 5 mm.

Preferably, at least some of the tissue-penetrating elements on the electrode member(s) will be retractable relative to a surface of the jaw upon which they are mounted. Usually, the tissue-penetrating elements will be arranged to reciprocate in and out of either or both of the jaws so that the jaws can be clamped over opposed surfaces of a target tissue region or mass with the elements retracted and the elements then penetrated into the tissue while the tissue remains clamped. In some instances, lines of reciprocating tissue-penetrating elements will define at least two and sometimes all of the electrode members. In other instances, they will form only one of the electrode members and/or they will be combined together with one or more elongate surface electrodes which engage but do not penetrate into the tissue.

The lines of tissue-penetrating elements may be on the same jaw or on different jaws. When the lines are on the same jaw, it is necessary to provide insulation so that each line is electrically isolated from the other, while the plurality of tissue-penetrating elements in an individual line remain electrically coupled. Electrical conductors will be provided within the shaft in order to permit attachment of each line to opposite polarity connections on an electrosurgical power supply. When present on different jaws, the lines of tissue-penetrating elements may be isolated from each other by maintaining appropriate electrical isolation between the jaws and/or at either or both ends of the tissue-penetrating elements.

The tissue-penetrating elements may have a wide variety of different configurations. Most commonly, they will be in the form of a pin or other rod-like tissue-penetrating electrode, usually having a sharpened distal end to facilitate penetration into tissue. Alternatively, an appropriate cutting current could be applied to the electrodes in order to facilitate tissue penetration while the jaws are being closed. Each line of tissue-penetrating elements may contain from 3 to 50 individual elements, usually from 6 to 25. The elements may extend over a length on the jaw(s) in the range from 1 mm to 50 mm, usually from 5 mm to 25 mm, with spacing between individual elements being in the range from 0.25 mm to 5 mm, usually from 0.5 mm to 2 mm. The distance between adjacent lines of tissue penetrating elements will usually be in the range from 0.5 mm to 10 mm, usually from 2 mm to 5 mm. The height of the tissue-penetrating elements (corresponding to the depth of tissue penetration) will usually be in the range from 1 mm to 10 mm, preferably from 2 mm to 5 mm, while the diameter of the elements will typically from 0.1 mm to 2 mm, usually from 0.5 mm to 1 mm.

In a more specific aspect of the present invention, the bipolar surgical instrument will comprise a shaft and a pair of opposed jaws, as generally described above. A first electrode member comprising a first line of tissue-penetrating elements will be disposed on one of the jaws and a second electrode member comprising a second line of tissue-penetrating elements will be disposed on one of the jaws. Either electrode members may be on the same jaw or on opposed surfaces of the two jaws. The first and second electrode members are electrically isolatable and laterally spaced-apart from each other. The bipolar device further includes a linkage attaching at least one of the jaws to the shaft. The linkage maintains opposed surfaces of the jaws in a generally parallel orientation as the jaws are moved between an opened and closed configuration by the linkage.

The linkage may be a parallelogram movement linkage, wherein actuation of the linkage by a clamp trigger on a handle attached to the proximal end of the shaft allows for parallel opening and closing of the jaws. The lines of tissue-penetrating elements will typically project toward the opposed jaw and lie parallel to each other as the jaws are opened and closed. The lines of tissue-penetrating elements (typically in the form of pins, needles, or other self-penetrating rods) may also be advanceable and retractable relative to a surface of the jaw upon which they are mounted by a knob on a handle attached to the proximal end of the shaft. Usually the knob will reciprocate the tissue-penetrating elements in and out of the jaw itself. In addition to protecting the tissue-penetrating elements and facilitating grasping of tissue (without the tissue-penetrating elements interfering when they are in the retracted position), reciprocation of the elements has the additional advantage of cleaning the tissue-penetrating elements during use. Frequently, charred tissue coagulated blood and/or other debris may foul the tissue-penetrating elements reducing their ability to effectively deliver high frequency electrical energy to the tissue. Reciprocation of the elements within the structure of the instrument will tend to shear debris from the surfaces of the tissue-penetrating elements (electrodes) to decrease surface resistance and impedance.

The instrument of the present invention may further comprise a cutting blade, knife, or other tissue-cutting structure disposed on one of the jaws. The cutting blade is actuatable to cut along a line between the first and second lines of tissue-penetrating elements by a cutting trigger on a handle attached to the proximal end of the shaft. In this way, the jaws can be clamped on tissue by pulling the clamping trigger, the tissue-penetrating elements penetrated into the tissue by knob advancement, the tissue treated electrosurgically by knob depression, and the tissue then cut between the two desiccated tissue regions by pulling the cutting trigger.

Optionally, either or both of the jaws may be perforated or otherwise provided with passages in order to permit the release of steam which is a byproduct of tissue heating. A rotational grip may also be attached between the proximal end of the shaft and a handle so as to allow for rotation of the shaft and the jaws relative to the handle. The rotational grip will usually permit rotation of the shaft and jaws up to about 90° in a clockwise and/or counter-clockwise direction from a centered position so as to facilitate loading and clamping of tissue by the jaws and to further minimize or prevent tissue deflection when the jaws are closed. A tissue stop may also be attached to one of the jaws of the present invention to prevent loading of tissue beyond the tissue-penetrating elements so as to ensure that only a target tissue region is clamped and treated.

In a more specific aspect of the method of the present invention, tissue is grasped between a first jaw and a second jaw, wherein opposed surfaces of the jaws are maintained in a generally parallel orientation. A first line of tissue-penetrating elements on one of the jaws and a second line of tissue-penetrating elements on one of the jaws is advanced through a surface of the jaw upon which they are mounted and into the tissue after grasping the tissue between the jaws. Clamping the tissue prior to advancing the tissue-penetrating elements protects the tissue-penetrating elements, i.e., from bending, and facilitates proper alignment of the tissue-penetrating elements into the tissue. The lines of tissue-penetrating elements will be parallel to and laterally spaced-apart from each other, generally as described above. A high frequency energy is then applied between a first line of tissue-penetrating elements on one of the jaws and a second line of tissue-penetrating elements on the same or a different jaw after advancing the lines of tissue-penetrating elements into the tissue.

A high frequency energy will preferably be applied to the tissue at a level and for a time sufficient to desiccate substantially all the tissue between the lines without causing substantial damage to other tissue, i.e., tissue outside of the lines. As described in greater detail in co-pending application Ser. No. 09/808,096, assigned to the assignee herein, the high frequency energy will be applied at a frequency in the range from 100 kHz to 2 MHz, preferably from 400 kHz to 500 kHz. The energy will be applied at a power from 5 W to 150 W, preferably from 10 W to 80 W, and for a time less than 5 minutes, usually from a range of 10 seconds to 1 minute. The power level may be increased at a predetermined rate from 1 W/sec to 100 W/sec, preferably from 1 W/sec to 10 W/sec. Usually, the high frequency energy will be terminated when an impedance of the tissue is in the range from 50 ohms to 1000 ohms, preferably from 250 ohms to 750 ohms.

The method of the present invention may further comprise rotating the jaws up to about 90° in a clockwise and/or counter-clockwise direction from a centered position prior to grasping the tissue between the jaws. This facilitates loading and clamping of tissue by the jaws and further minimizes or prevents any tissue deflection when the jaws are closed. Further, the grasping force applied to the tissue by the first and second jaws may be limited so that only sufficient force to clamp the tissue is applied. The method may also include cutting the tissue along a line between the first and second lines of tissue-penetrating elements after the tissue has been substantially desiccated. It will be appreciated that the tissue is still grasped between the jaws and the tissue engaged by the tissue penetrating elements so as to facilitate proper alignment of the desiccated tissue during cutting. The lines of the tissue-penetrating elements are then retracted prior to disengaging the jaws after treatment to prevent any tearage of tissue.

BRIEF DESCRIPTION OF THE DRAWINGS

FIG. 16E illustrates an isolated view of an exposed lower jaw of FIG. 15 with an advanced cutting blade.

DESCRIPTION OF THE SPECIFIC EMBODIMENTS

Figure 1A:
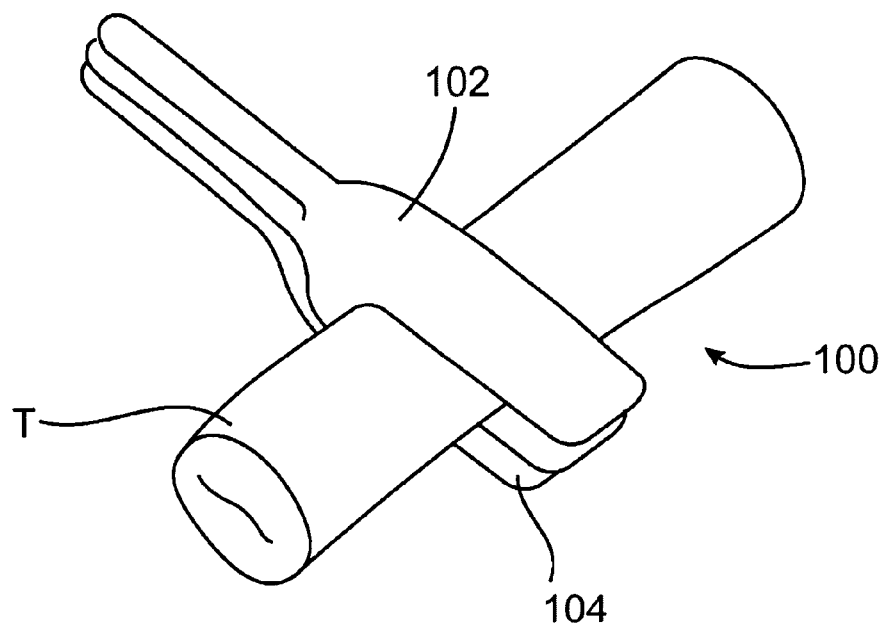
FIGS. 1A and 1B illustrate use of conventional bipolar forceps for coagulating a tubular structure in the body.

According to the present invention, bipolar surgical instruments will include at least two and up to four or more laterally spaced-apart electrode members disposed on a pair of actuable jaws. By properly positioning the electrode members relative to each other, radiofrequency energy applied to tissue disposed between the jaws can be focused within a well-defined region between the electrode members. In contrast to prior art devices and methods, where electrodes of opposite polarity are generally engaged against directly opposed tissue surfaces, the present invention will position at least one positive electrode and at least one negative electrode on and/or into laterally spaced-apart sites on opposed tissue surfaces.

The electrode members may be configured in a wide variety of patterns and designs, some of which are illustrated in FIGS. 2A–2E. Most simply, one jaw 200 may carry a first electrode member 202 which is laterally spaced-apart from a second electrode member 204, where the electrode members are connectable to opposite poles of a power supply. An opposed jaw 206 may be free from electrodes of any sort. The jaws 200 and 206 will be actuable, as described in more detail hereinafter, so the tissue may be grasped between two opposed tissue-engaging surfaces 208 and 210. When tissue is grabbed between the jaws 200 and 206, current flow will be generally limited to between the electrode members 202 and 204.

Figure 2A:
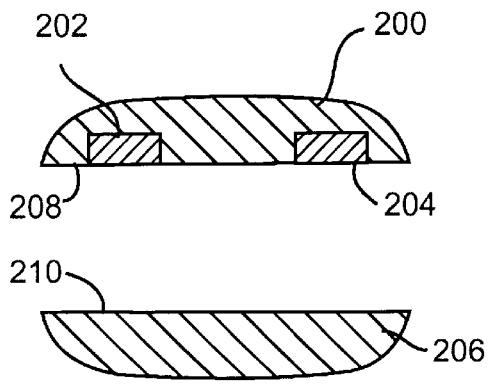
FIGS. 2A–2F illustrate a plurality of alternative electrode configurations according to the present invention.
Figure 2D:
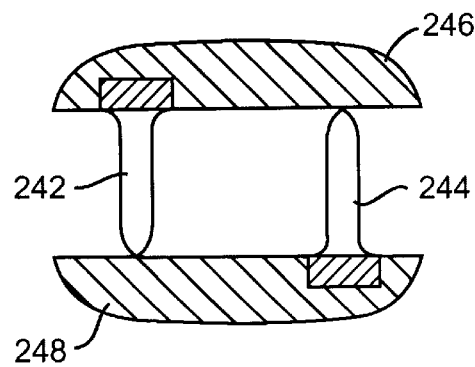
Figure 2B:
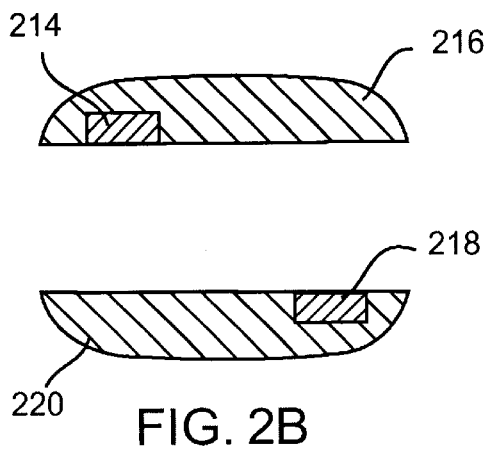

While the electrode member configuration of FIG. 2A is functional, the current flow pattern between the electrodes can be improved by having a first electrode member 214 on a first jaw 216 and a second electrode member 218 on a second jaw 220 as illustrated in FIG. 2B. As with the configuration of FIG. 2A, the electrode members 214 and 218 of FIG. 2B will generally limit current flow so that it does not extend significantly to tissue outside the lateral boundaries of the jaws 216 and 220. By placing the electrode members 214 and 218 on opposed jaws, enhanced current flow through the tissue may be achieved.

Figure 2E:
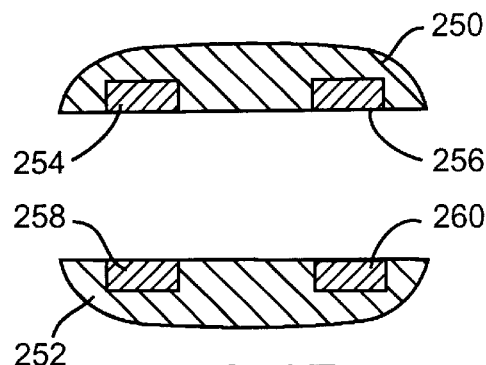
Figure 2C:
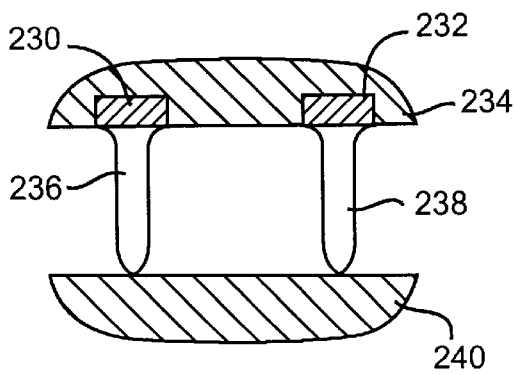

A further alternative improved configuration of the electrode members according to the present invention is illustrated in FIG. 2C. First electrode member 230 and second electrode member 232 are each carried on a first jaw 234, in a manner similar to the embodiment of FIG. 2A. The electrode members 230 and 232, however, each include a line of tissue-penetrating elements thereon. The electrode members 202 and 204 in FIG. 2A are generally linear electrodes having a width and length within the ranges set forth above. Such electrodes will form a flat contact or interface with the tissue which is engaged between the jaws 200 and 206. By providing tissue-penetrating elements 236 and 238, as illustrated in FIG. 2C, two advantages are achieved. First, the total electrode area in contact with the tissue can be greatly enhanced, typically from two-fold to 10-fold, or greater. Moreover, by extending the electrode "boundaries" into the tissue, the ability to achieve uniform current flux within the tissue is improved and the containment of that current flux within the target region is also enhanced. The embodiment of FIG. 2C will include an opposed jaw 240 which is free from electrodes.

A slightly modified configuration for tissue-penetrating elements 242 and 244 is illustrated in FIG. 2D. Instead of carrying both lines of tissue-penetrating elements 242 and 244 on a single jaw, the first line 242 is carried on an upper jaw 246 and the second line 244 is carried on a lower jaw 248. The advantages regarding increased electrode area and current flux containment, however, are generally comparable to those achieved with the embodiment of FIG. 2C.

Yet another alternative for the electrode member configuration is illustrated in FIG. 2E. Jaws 250 and 252 each carry pairs of laterally spaced-apart members 254, 256, 258 and 260. The electrode members can be adapted for connection to a power supply so that laterally spaced-apart pairs of electrodes will have opposite polarity when the instrument is powered. For example, electrodes 254 and 258 may have a first polarity while electrodes 256 and 260 may have a second polarity. Alternatively, but less preferably, electrodes 254 and 260 may have a first polarity while electrodes 258 and 256 may have a second polarity. The latter configuration will be generally less effective at containing current flow than the former configuration since pairs of oppositely energized electrodes will directly oppose each other when the instrument is engaged against tissue.

Figure 2F:
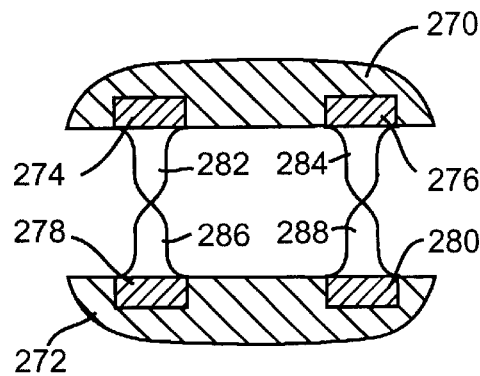

Yet another electrode configuration is illustrated in FIG. 2F. There, each jaw 270 and 272 carries a pair of electrode members 274, 276, 278, 280. Each of the electrode members, in turn, carries a line of tissue-penetrating elements 282, 284, 286, 288. The tissue-penetrating elements are arranged so that their distal tips will engage each other when the jaws 270 and 272 are closed together. Opposed pairs of electrode members 274/278 and 276/280 will have the same polarity, i.e., the laterally spaced-apart pairs will be of opposite polarity. In many ways, the operation of the embodiment of FIG. 2F will be the same as that of both FIG. 2C and FIG. 2D. The embodiment of FIG. 2F may also be modified by axially spacing apart the opposed penetrating elements 282/286 and 284/288 so that the elements penetrate fully to the opposed jaw 270 or 272. A variety of other electrode modifications will also be possible within the scope and spirit of the present invention.

Figure 3A:
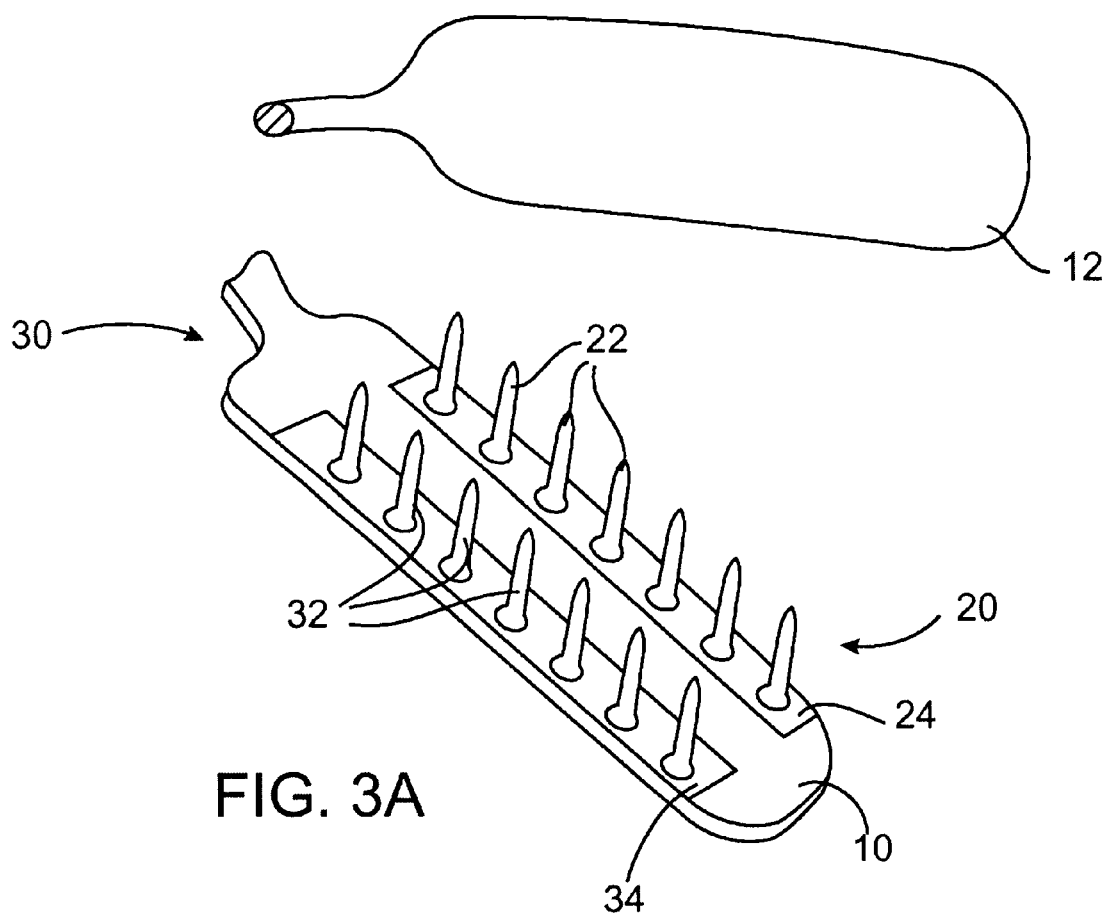
FIG. 3A is a perspective view of a pair of actuable jaws carrying two lines of electrically coupled tissue-penetrating elements in accordance with the principles of the present invention.
Figure 3B:
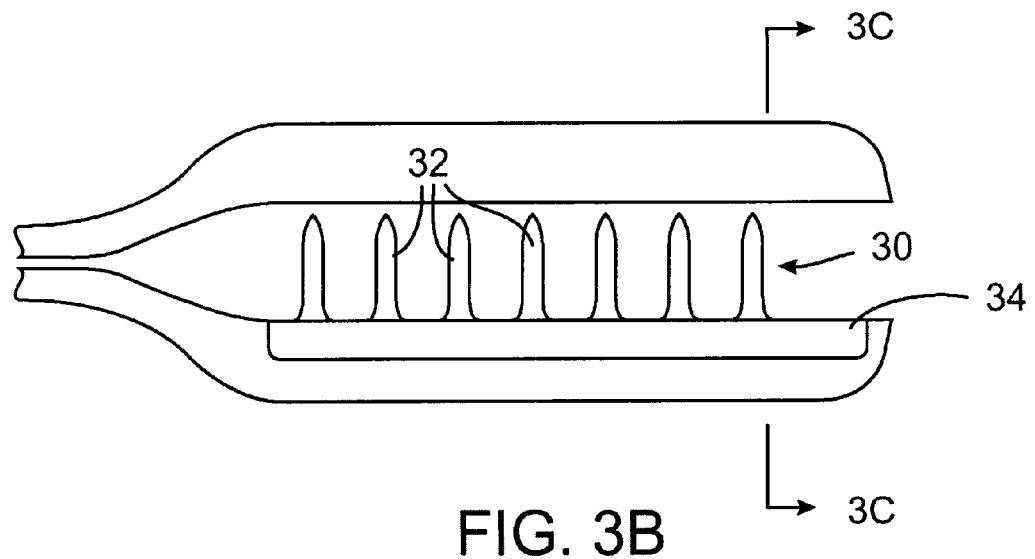
FIG. 3B is a side, elevational view of the jaws of FIG. 1, shown with the jaws closed.
Figure 3C:
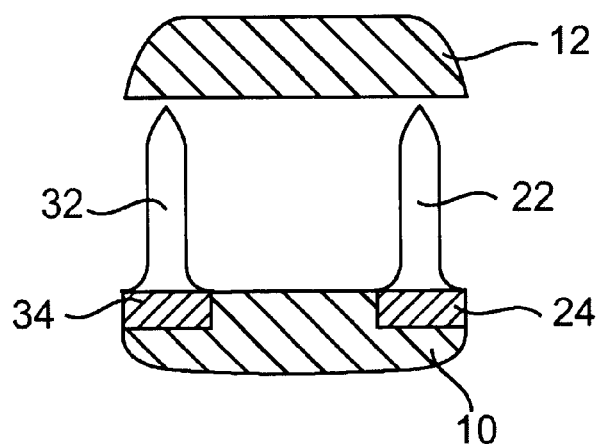
FIG. 3C is a cross-sectional view taken along line 3—3 of FIG. 2.

Referring now to FIGS. 3A–3C, a first pair of jaws 10 and 12 which may be utilized for grasping tissue and applying high frequency energy according to the methods of the present invention will be described. The jaws 10 and 12 will be actuable or reciprocatable in a manner conventional for forceps, graspers, and other similar types of medical devices. Specific shaft designs which provide for such actuation will be described hereinafter in connection with FIGS. 5–7.

A first line 20 comprising seven tissue-penetrating pins 22 is disposed on one side of the lower jaw 10 and a second line 30 of tissue-penetrating pins 32 is disposed on the other side of the lower jaw. The first line 20 of pins 22 is electrically coupled by an electrically conductive strip 24 into which the pins are attached. Similarly, a second electrically conductive strip 34 is disposed on the other side of the jaw and electrically couples the second line 30 of pins 32. Each of the electrically conductive strips 24 and 32 will be attached to conductors (not shown) which extend proximally down the shaft of the device and which provide for electrical attachment of the lines 20 and 30 to a conventional electrosurgical power supply.

The electrically conductive strips 24 and 34 will be electrically isolated from each other. For example, the strips 24 and 34 may be imbedded in an insulating material, such as a ceramic, plastic, or the like. Alternatively, an insulating layer may be formed around the strips 24 so that they are electrically isolated from the lower jaw 10. The upper jaw 12 may also be formed from a ceramic or other electrically insulating material to assure that the pins 22 and 32 are not shorted by contact with the upper jaw. The pins 22 and 32 and strips 24 and 34 will be formed from an electrically conductive material, typically a metal such as stainless steel, gold, silver, or the like. The dimensions, number, spacing, and other characteristics of the pins 22 and 32 will be within the ranges set forth above. While shown in a straight line, the pins 22 and 32 could also be arranged in the other patterns set forth above.

Figure 4:
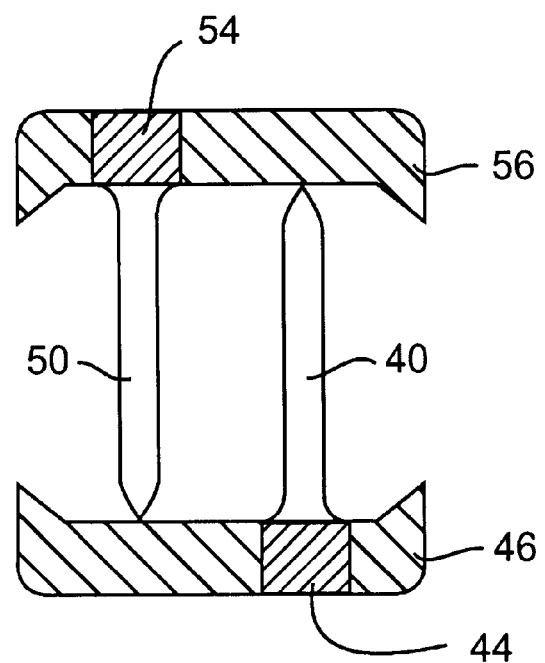
FIG. 4 is an alternative cross-sectional view of a pair of jaws constructed in accordance with the principles of the present invention.

The embodiment of FIGS. 3A–3C shows both lines 20 and 30 of tissue-penetrating elements 22 and 32 being connected to the same jaw. The present invention would also cover embodiments where the lines of tissue-penetrating elements are connected to opposite jaws, as shown in FIG. 4. There, a first line of pins 40 are mounted within a conductive strip 44 in a lower jaw 46, while a second line of tissue-penetrating elements 50 are mounted in an electrically conductive strip 54 in an upper jaw 56. The individual tissue-penetrating elements 40 and 50 are thus coupled to each other within each line, but the two lines are electrically isolated, so that the result is a pair of electrically isolated lines of tissue-penetrating elements, as with the first embodiment.

Figure 5:
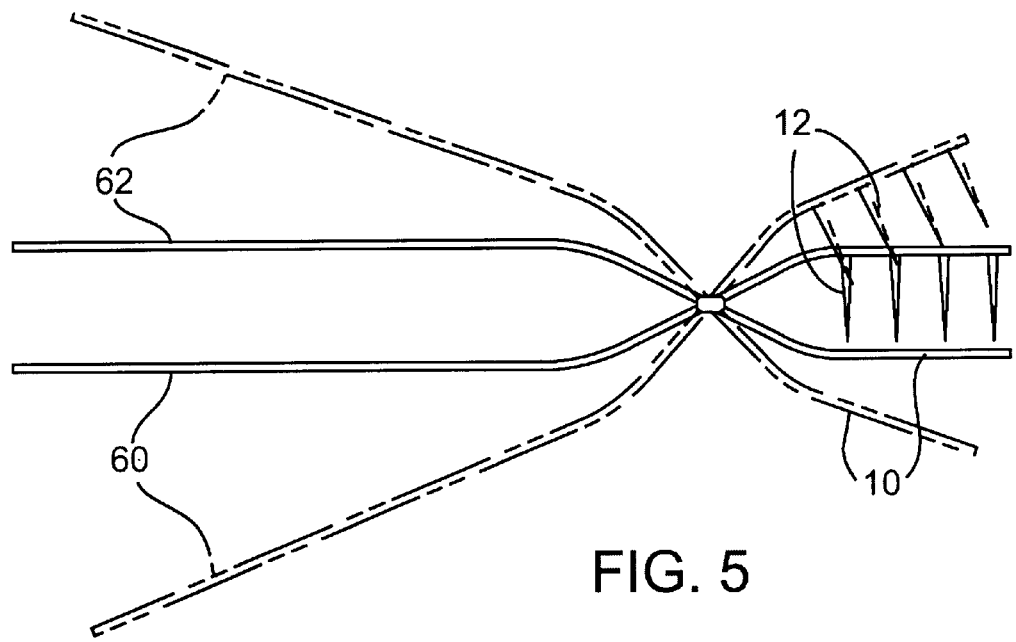
FIG. 5 illustrates a scissors-type actuating mechanism that can be used with the jaws of FIG. 1.
Figure 6:
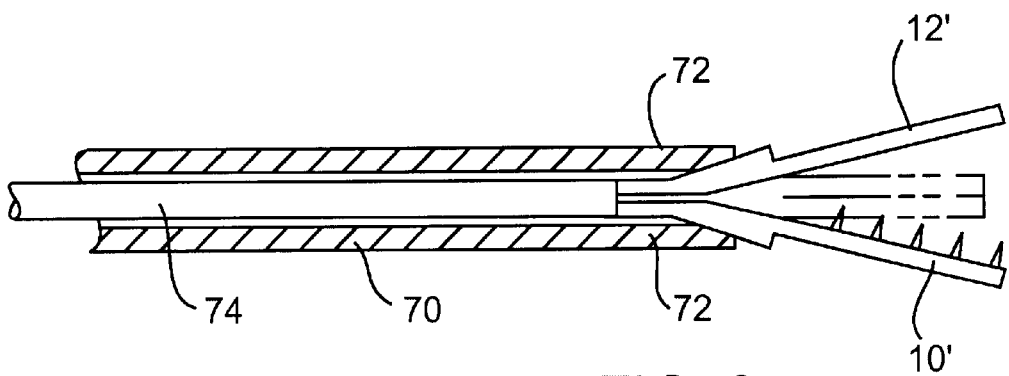
FIG. 6 illustrates a pair of resiliently-mounted jaws that can be opened and closed with a cam surface, where the jaws incorporate tissue-penetrating elements according to the principles of the present invention.
Figure 7:
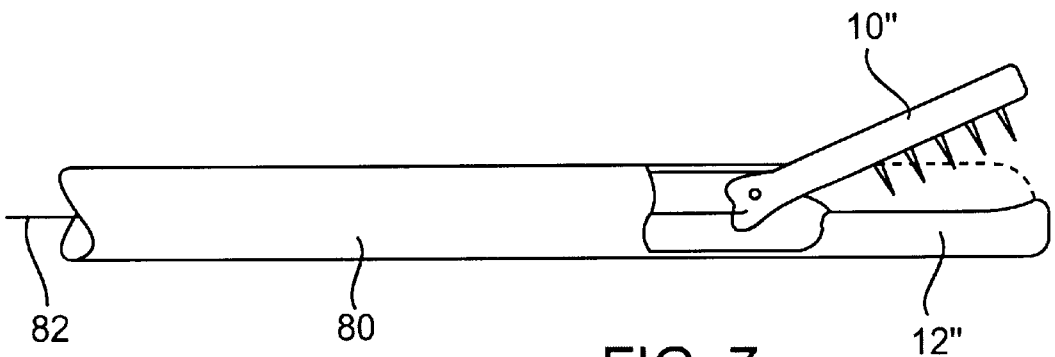
FIG. 7 illustrates an alternative jaw actuating mechanism which may be utilized in the devices of the present invention.

Referring now to FIGS. 5–7, the present invention can rely on virtually any jaw-actuating mechanism of a type utilized in medical devices. For example, the mechanism can be a simple scissors mechanism, as shown in FIG. 5, where the jaws 10 and 12 are pivotally connected to actuating levers 60 and 62. The mechanism may alternatively comprise camming mechanisms, linear/pivot actuators, or the like. Opening and closing of the levers 60 and 62 will open and close the jaws in a conventional manner.

Jaws 10' and 12' can also be mounted within a hollow tube 70 having cam surfaces 72 formed at its distal end. The jaws 10' and 12' are resiliently mounted on a rod 74 so that the jaws may be axially translated relative to the cam surfaces 72 to open the jaws (as shown in full line) and close the jaws (as shown in broken line) in FIG. 6.

As a third common alternative, jaws 10" and 12" may be formed at the distal end of a tubular actuator 80. The jaw 10" which is free from tissue-penetrating elements is integrally formed at the end of the tube 80. The moveable jaw 10" having the tissue-penetrating elements is pivotally attached and is actuated by a rod 74 or cable 82 extending to a proximal end of the device (not shown).

The assemblies of FIGS. 6 and 7 may be manually operated by conventional proximal assemblies (not shown), such as three-ring actuators, pistol grips, or any other actuator which permits linear movement of the rod 74 or cable 82. The devices of FIGS. 6 and 7 would be particularly useful for laparoscopic, thoracoscopic, arthroscopic, or other procedures where they are to be introduced through narrow diameter cannulas, typically having shaft diameters below 12 mm, more typically below 10 mm, and sometimes 5 mm or smaller.

Figure 1B:
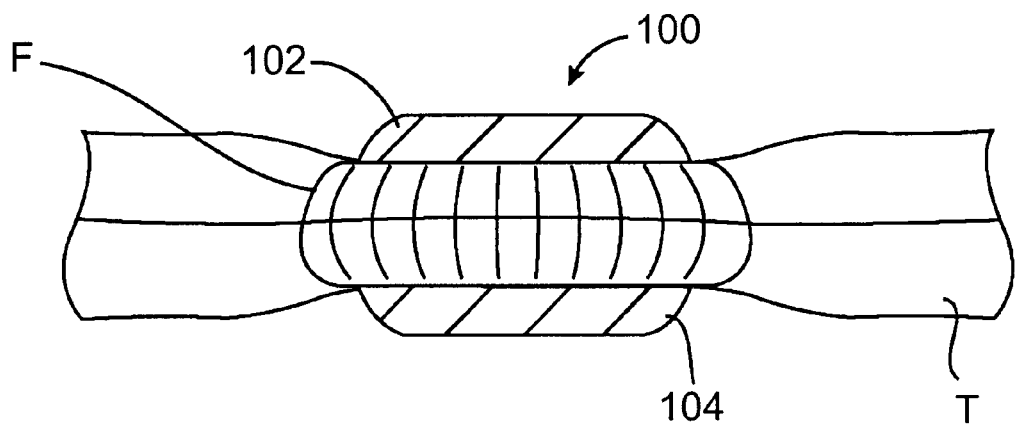
Figure 8:
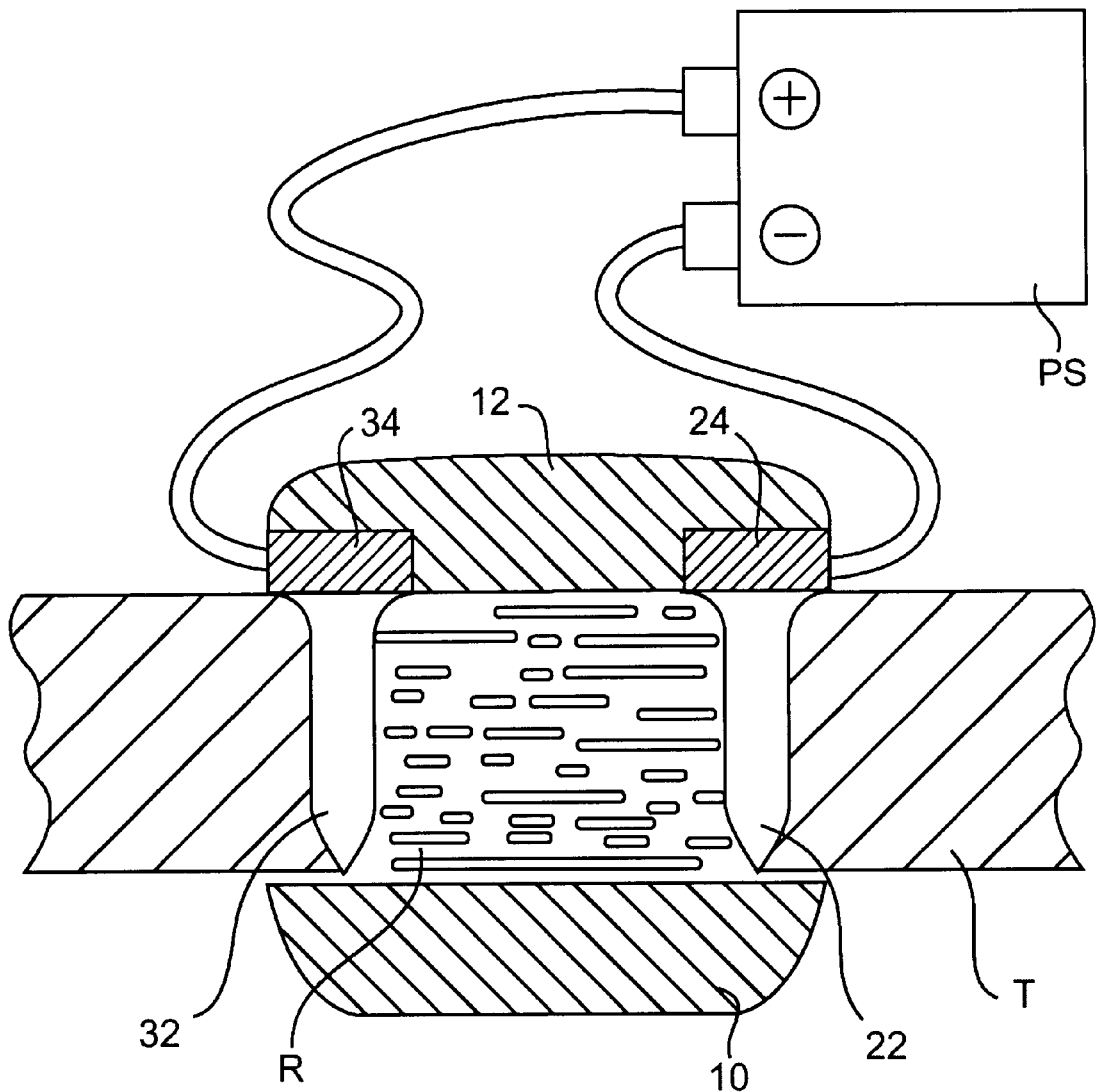
FIG. 8 illustrates use of the jaws of FIG. 1 in treating tissue according to the method of the present invention.

Referring now to FIG. 8, use of the jaws 10 and 12 of FIGS. 1–3 for treating tissue T is illustrated. The jaws 10 and 12 are actuated to grasp a tissue structure, such as an artery, vein, fallopian tube, ligament, or other tubular or elongate structure therebetween. The tissue-penetrating elements 22 and 32 pierce and penetrate into the tissue T to create a region R therebetween. The electrically conductive strips 24 and 34 are attached to an external power supply PS so that they may be energized with opposite polarities. Suitable power supplies are available from commercial suppliers, such as Valleylab, Aspen, and Bovie. The power supplies may operate with conventional sinusoidal or non-sinusoidal wave forms and may operate at fixed or controlled power levels, where voltage, current, or both may be selected. When energized at the power levels, frequencies, and durations described above, the tissue region R between the lines of penetrating elements 22 and 32 will receive a high flux of energy, causing heating, coagulation, and optionally necrosis of the tissue. Heating of the adjacent tissues outside of this region R is minimal.

Figure 9A:
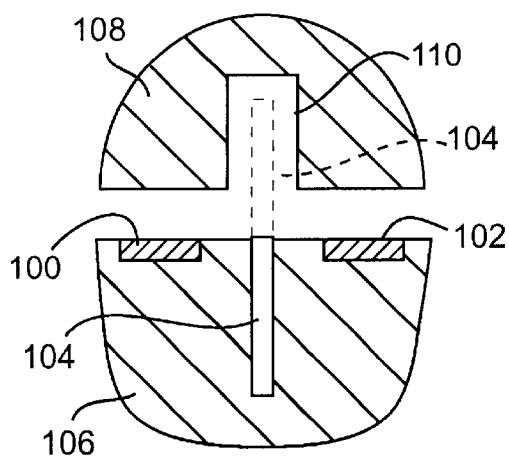
FIGS. 9A–9F illustrate a plurality of alternative reciprocating electrode configurations according to the present invention.
Figure 9B:
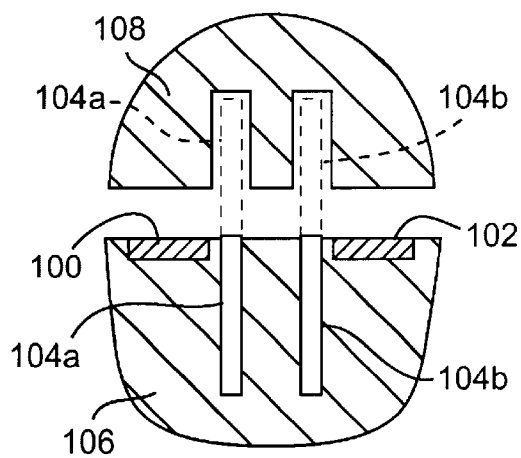
Figure 9C:
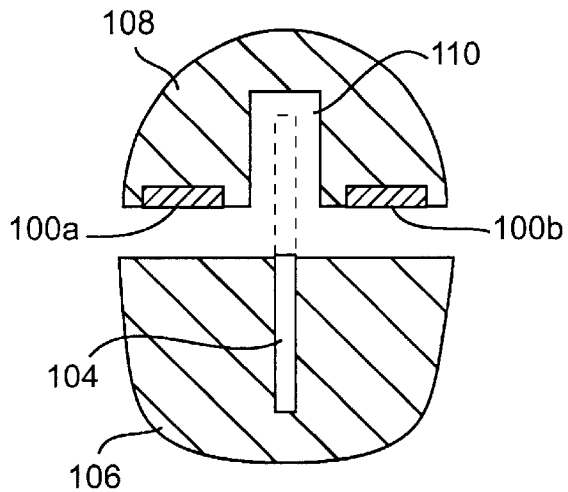
Figure 9D:
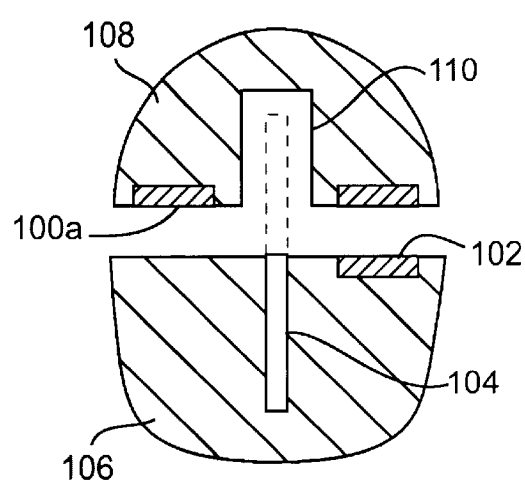
Figure 9E:
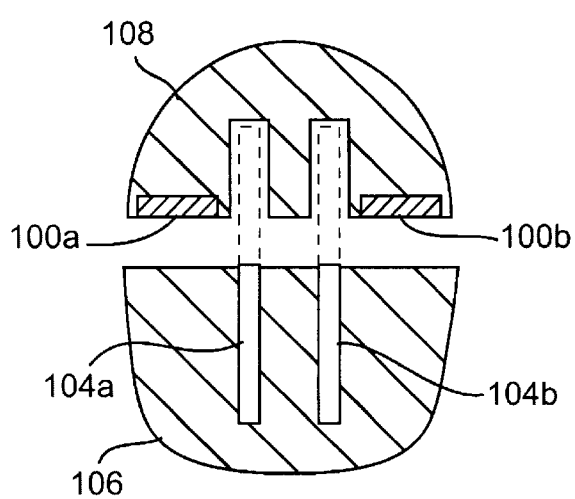
Figure 9F:
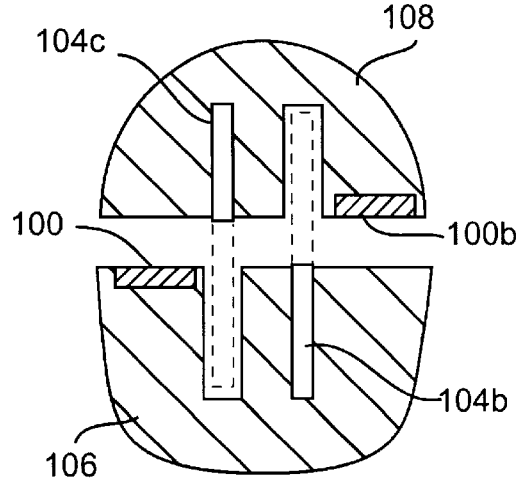

Referring now to FIGS. 9A–9F further electrode configurations will be described. In particular, at least some of the electrode structures may include or consist of a line of tissue-penetrating elements, usually in combination with non-penetrating surface electrodes. Preferably, a pair of laterally spaced-apart elongate surface (non-penetrating) electrodes 100 and 102 will be disposed on opposite sides of a line of reciprocating tissue-penetrating elements 104, as illustrated in FIG. 9A. FIG. 9A is a cross-sectional view where only a single tissue-penetrating element is illustrated. It will be appreciated that a plurality of elements are formed in a line down the length of jaw 106. Similarly, the elongate electrodes 100 and 102 extend along the length of the jaw. An upper jaw 108 is provided to permit tissue clamping, and a channel 110 is formed in the upper jaw to accommodate penetration of the elements 104, as shown in broken line. FIG. 9B illustrates an instrument similar to that shown in FIG. 9A, except that there are two lines 104a and 104b of tissue-penetrating elements positioned between the elongate surface electrodes 100 and 102. The configuration of the instrument shown in FIG. 9C is also similar to that of FIG. 9A, except that the elongate surface electrodes 100a and 100b have been moved to the upper jaw structure 108. FIG. 9 illustrates yet another configuration where a first elongate surface electrode 100a is on the upper jaw structure 108 and a second elongate surface electrode 102 is on the lower jaw structure 106. FIGS. 9E and 9F illustrate instrument configurations having a pair of tissue-penetrating element lines. In FIG. 9E, the lines 104a and 104b are disposed in the lower jaw structure 106, while the elongate surface electrodes 100a and 100b are in the upper jaw structure 108. FIG. 9F illustrates a configuration where a first elongate surface electrode and a second line 104b of tissue-penetrating elements are in the lower jaw structure 106 while a second elongate surface electrode 100b and a first line 104c of tissue-penetrating elements are in the upper jaw structure 108.

As can be seen from above, the relative positions of reciprocating (and non-reciprocating) tissue-penetrating elements and elongate surface electrodes (non-penetrating electrodes) can vary widely. In addition, the numbers of elements provided on any surgical instrument can also vary. At a minimum, there will be at least one line of tissue-penetrating elements and one other electrode structure, either tissue penetrating or tissue non-penetrating. The two electrode structures will be elongate, i.e., will have a minimum length dimension of at least 1 mm, more usually being in the range from 5 mm to 25 mm. In the illustrated embodiments, the electrode structures are shown as being generally linear. Other configurations will also be possible, such as concentric, non-linear, serpentine, or the like. The lateral distance between parallel electrode lines, however, will generally remain constant, typically being in the range from 0.5 mm to 10 mm, more usually from 1 mm to 5 mm. The dimensions of the tissue-penetrating elements have been set forth above. The elongate surface electrodes will typically have widths in the range from 0.1 mm to 5 mm, preferably from 0.5 mm to 3 mm. While the surface electrodes are illustrated as being flat, it is also possible that they would have irregular surfaces, possibly to improve electrical contact. The surface irregularities, however, should be such that there is little or no tissue penetration since it is a purpose of the outer surface electrode structures to seal the edges of the tissue being treated and to avoid possible bleeding which could be caused by the introduction of the tissue-penetrating elements.

Figure 10A:
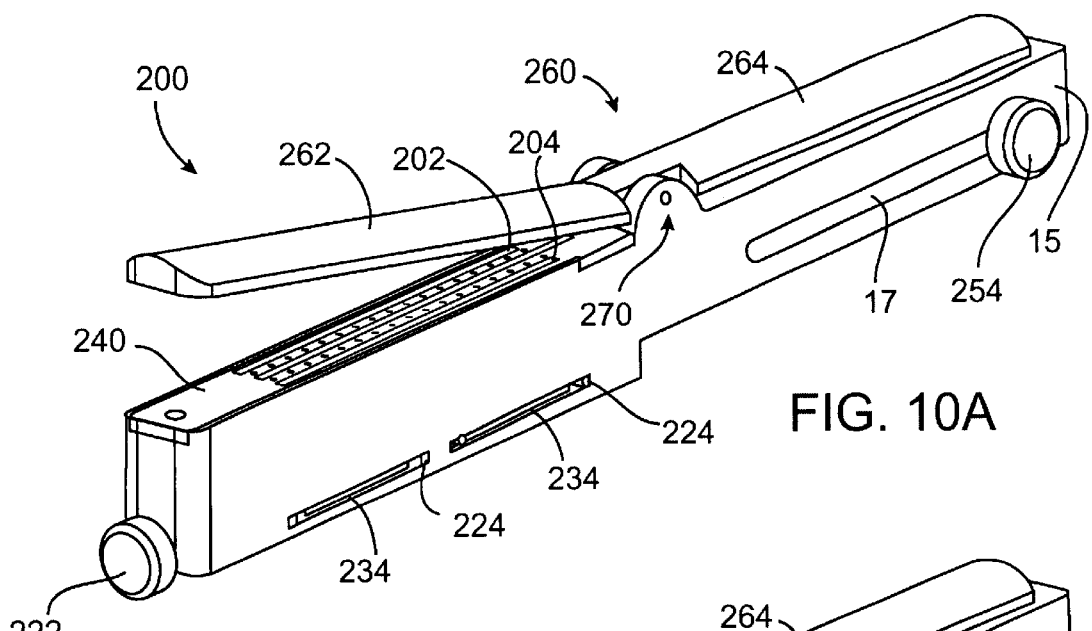
FIGS. 10A–10C illustrate an alternative bipolar surgical instrument constructed in accordance with the principals of the present invention and employing reciprocating electrode lines.
Figure 10B:
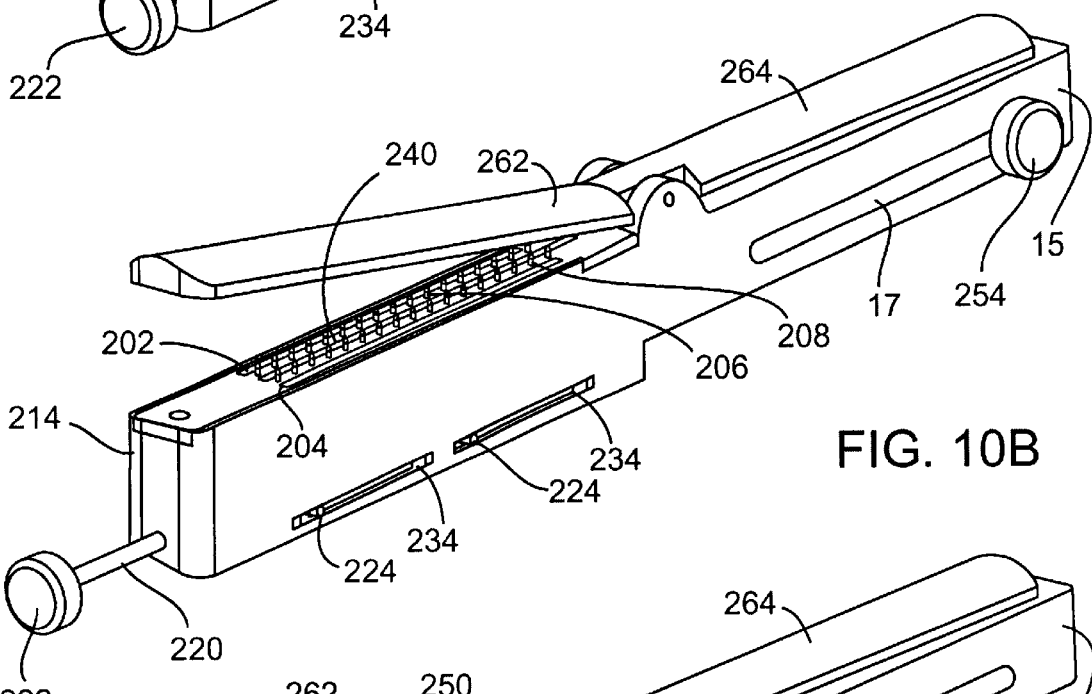

Referring now to FIGS. 10A–10C, 11, 12A, 12B, and 13, a bipolar surgical instrument 200 having an arrangement of surface electrodes 202 and 204 and tissue-penetrating electrodes and lines 206 and 208 of tissue-penetrating electrodes, is illustrated. In lines 206 and 208 of tissue-penetrating electrodes are mounted in an electrically conductive insert 210 (FIG. 13) which in turn is mounted in a cavity 212 in instrument housing 214. The insert 210 is free to reciprocate within the cavity 212 and is mounted on a rod 220 having a knob 222 and a pair of pins 224. The rod 220 is received in a channel 230 in the bottom of insert 210, and the pins 224 extend outwardly through a pair of inclined slots 232 in the insert and then through slots 234 in the side of the housing 214. In this way, axial movement of the rod 220 (caused by pulling or pushing on the knob 222) can cause the insert 210 to rise or lower within the cavity 212. In turn, this causes the tissue-penetrating electrodes 206 and 208 to reciprocate between a lowered configuration (FIG. 10A) and a raised configuration (FIG. 10B).

Figure 10C:
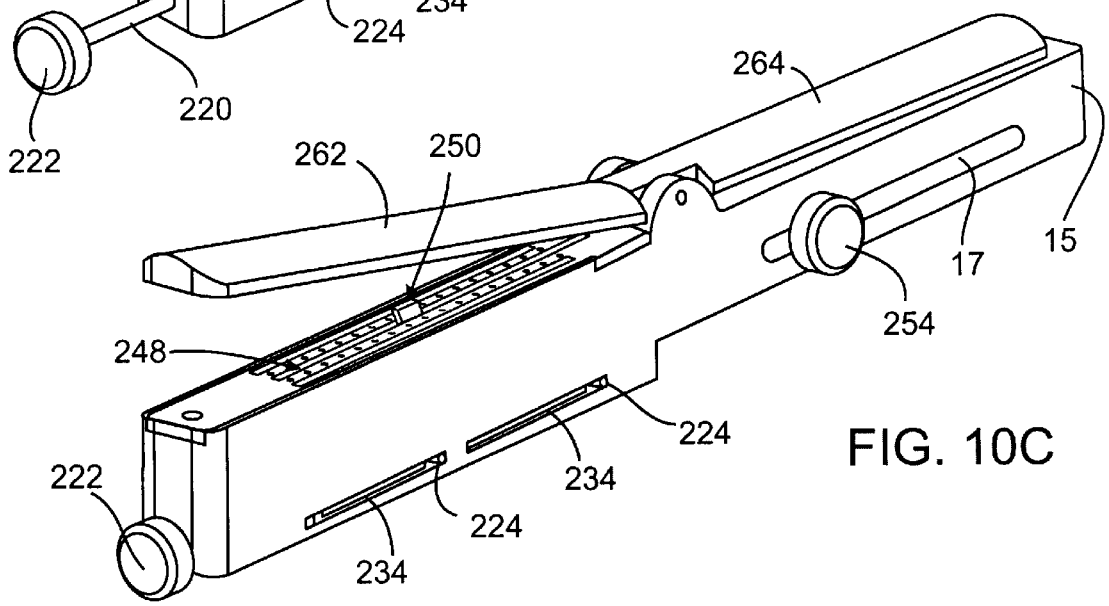

The elongate surface electrodes 202 and 204 are received in an electrically insulating plate 240 which is mounted over the cavity 212 in housing 214. The plate 240 has a pair of slots 242 and 244 for receiving the electrodes 202 and 204, respectively. Additionally, plate 240 has a plurality of holes 246 along the lines spaced inwardly from the slots 242 and 244, respectively. Additionally, a channel 248 is formed along the center line of the plate 240 to receive a cutting blade 250, as best seen in FIG. 10C.

Figure 11:
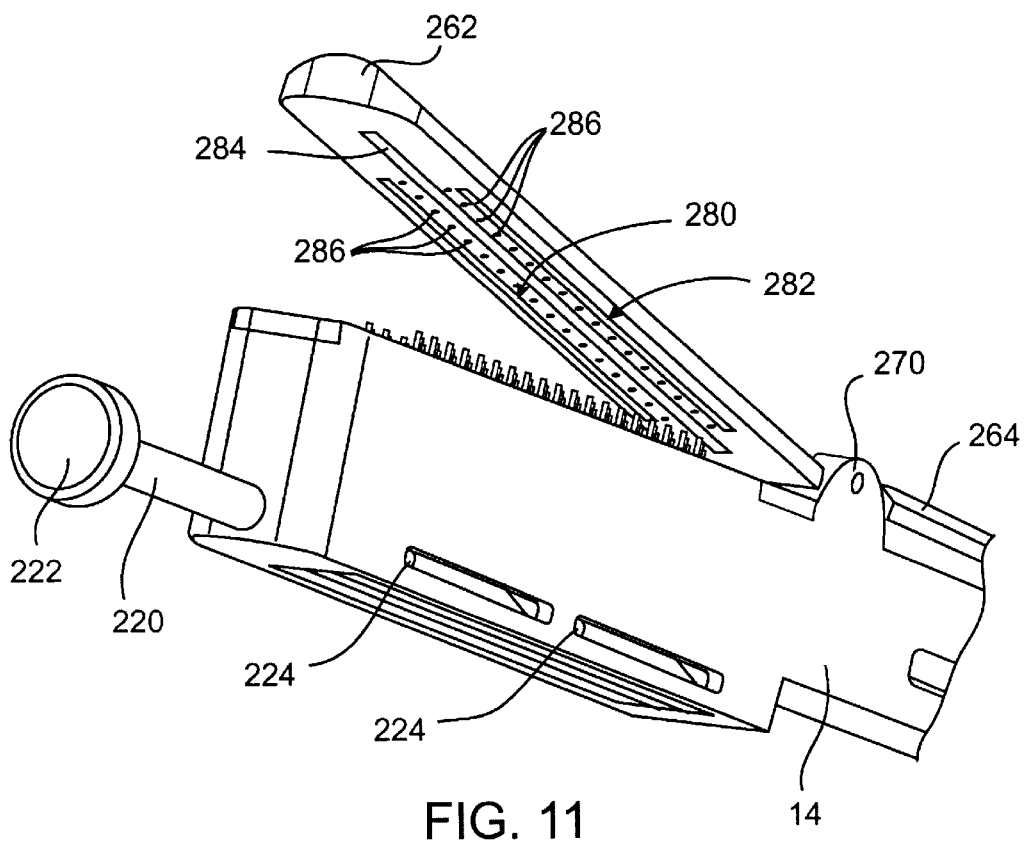
FIG. 11 is an alternative view of the device of FIGS. 10A–10C.

The housing 214 forms a lower jaw structure and a hinged lever assembly 260 forms the upper jaw structure. The lever 260 includes a cover section 262 and a lever arm section 264. A center or fulcrum section 266 is secured between brackets 270 formed on the top of housing 214. In this way, the cover section 262 can be moved between an open configuration (FIG. 10A) and a closed configuration (FIGS. 14B and 14C) by lifting and lowering the lever arm section 264. The bottom of the cover section 262 is best illustrated in FIG. 11. The bottom includes a pair of top surface electrodes 280 and 282, a relief channel 284 for receiving the cutting blade 250, and relief holes 286 for receiving the upper tips of the tissue-penetrating electrodes when they are raised.

The cutting blade 250 is formed at a forward end of an elongate blade structure 252 having a pair of knobs 254 at its opposite or proximal end. The body portion 252 of the blade is received in a slot 258 in a handle portion 15 of the housing 14. The knobs extend on a connecting shaft out through a slot 17 in the handle 15. Thus, the blade can be advanced and retracted axially by moving the knob 254 from a retracted configuration (FIGS. 10A and 10B) to an advanced configuration (FIG. 10C). The knob is disposed in the channel 248 so that it will pass and cut through tissue which has been previously necrosed by applying high frequency energy through the electrode structures, as described below.

Figure 12A:
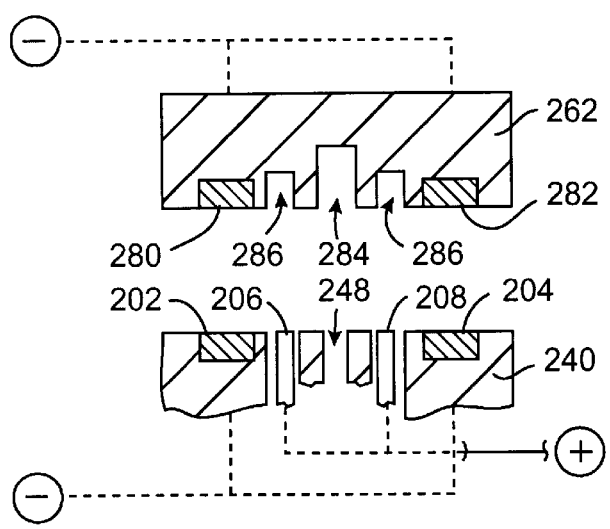
FIGS. 12A and 12B illustrate the relative positions of the various electrode structures in the device of FIGS. 10A–10C.
Figure 12B:
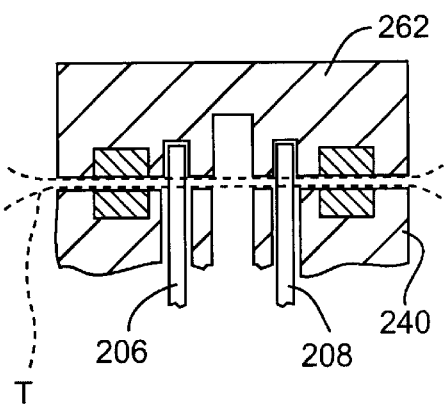
Figure 13:
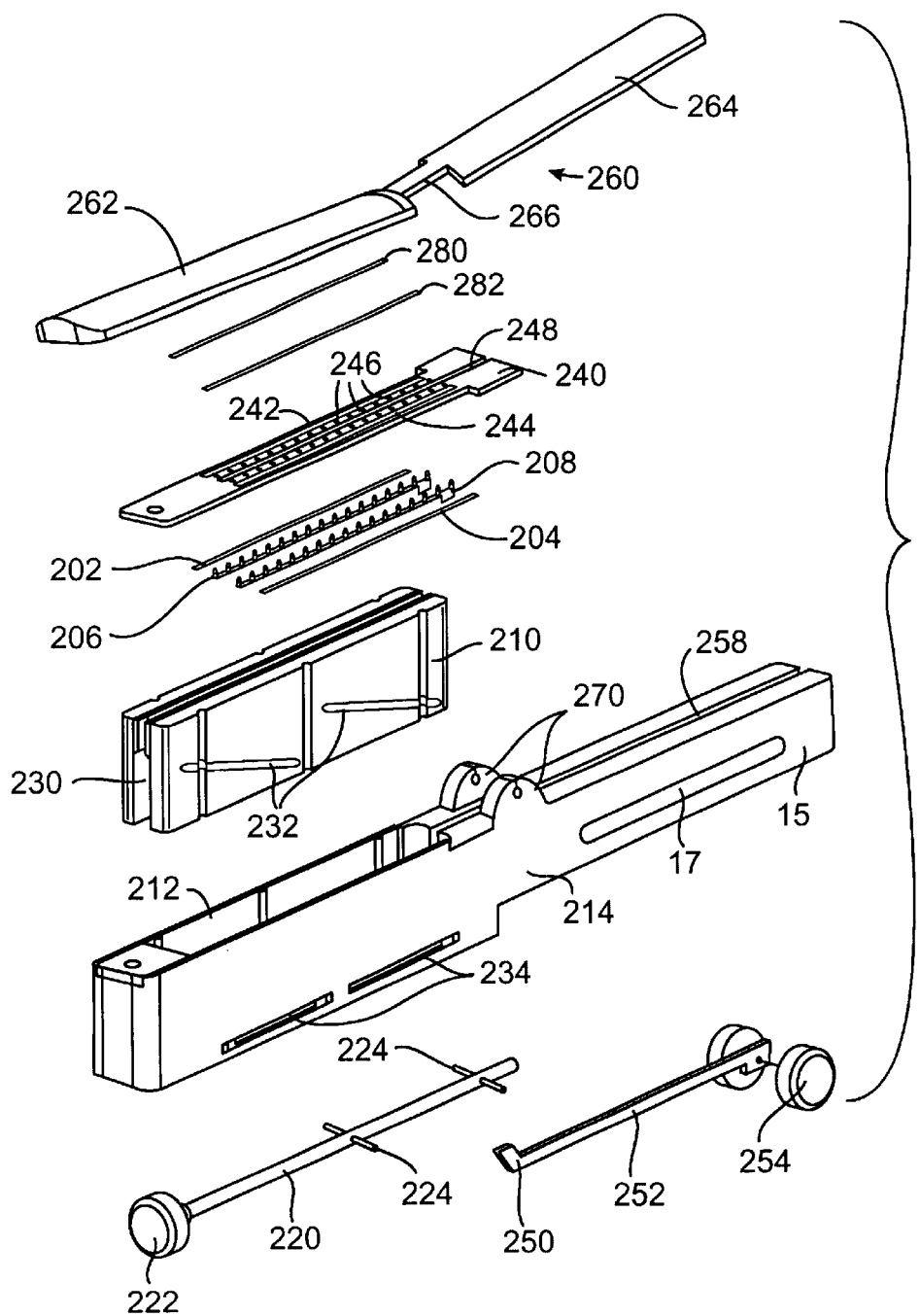
FIG. 13 is an exploded view of the device of FIGS. 10A–10C.
Figure 14A:
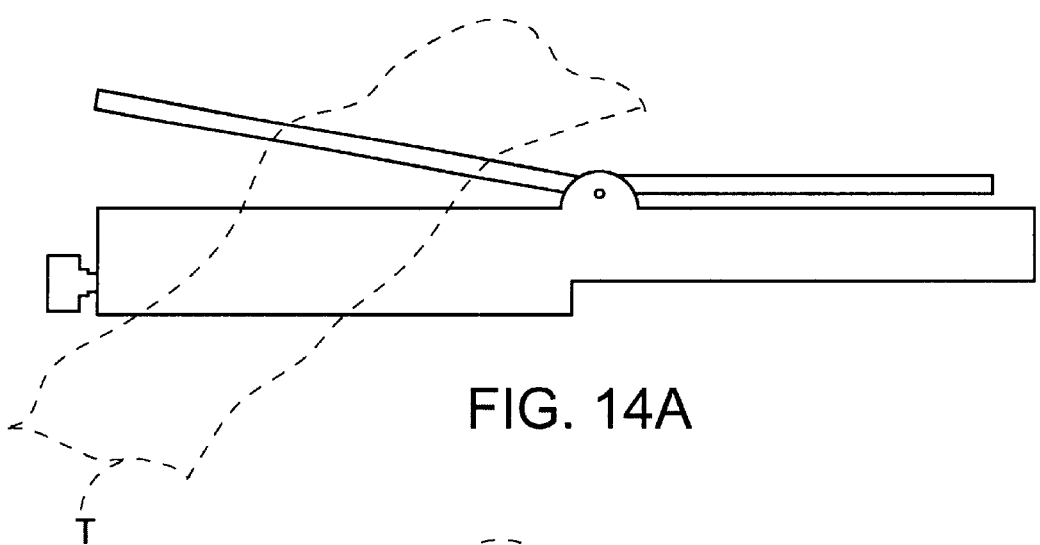
FIGS. 14A–14C illustrate use of the device of FIGS. 10A–10C in applying high frequency electrical energy to tissue.
Figure 14B:
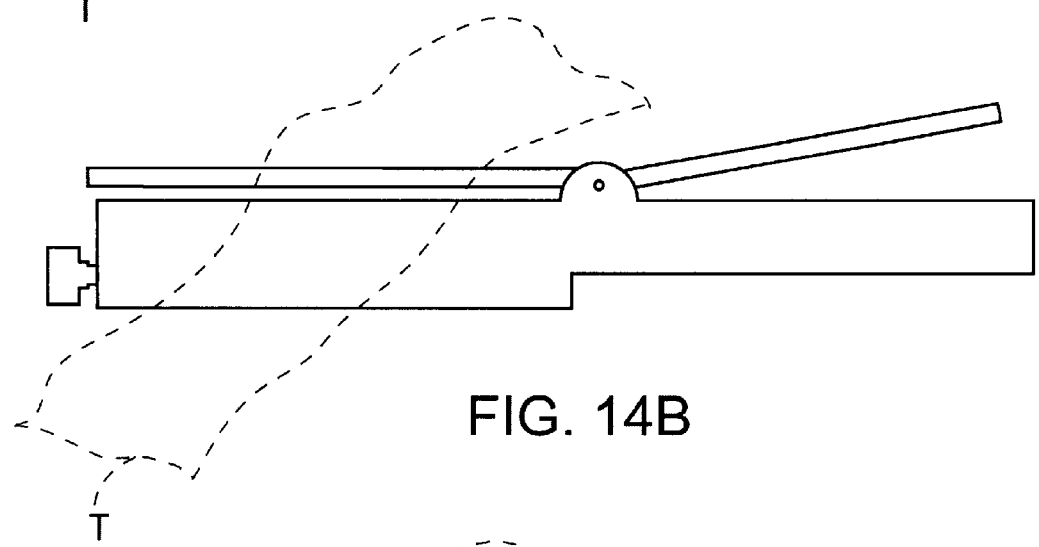
Figure 14C:
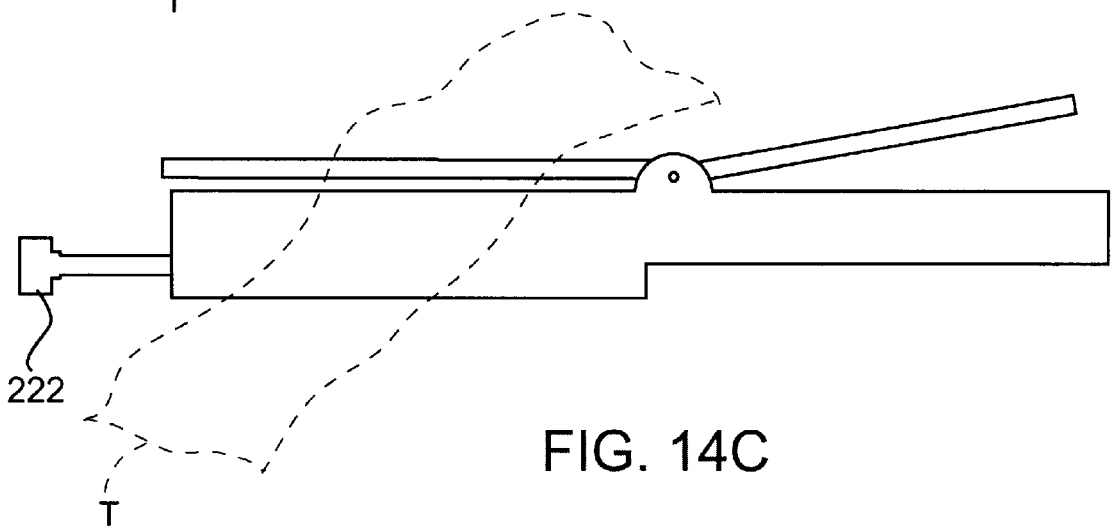

Referring now to FIGS. 12A and 12B, the interrelationship of the various electrode structures and instrument 200 will be described. Initially, the cover 262 will be open and the tissue-penetrating electrodes 206 and 208 retracted into the housing 14, as shown in FIG. 12A. After positioning a target tissue structure between the open cover 262 and plate 240 of the housing 14 (as shown in FIG. 14A), the cover can be closed capturing the tissue (as shown in FIGS. 12B and 14B). The tissue-penetrating electrodes are then raised by pulling knob 222 (FIGS. 12B and 14C), causing the electrodes 206 and 208 to penetrate the tissue. Surface electrodes 202, 204, 280, and 282 in contrast, will compress on opposite sides of the tissue, but will not penetrate into the tissue. Radiofrequency or other high frequency electrical energy will then be applied to the tissue, with the surface electrodes being attached to one pole of a suitable power supply and the tissue-penetrating electrodes being attached to the other pole. The electrical field will thus be concentrated between an outermost pair of surface electrodes (202/280 or 204/282) and the adjacent tissue-penetrating electrode (206 or 208). The tissue may be fully necrosed with all the advantages of the use of a tissue-penetrating electrode as described above. After adequate necrosis is achieved, the blade 252 can be advanced to cut through the parallel segments of necrosed tissue which have been formed.

Figure 15:
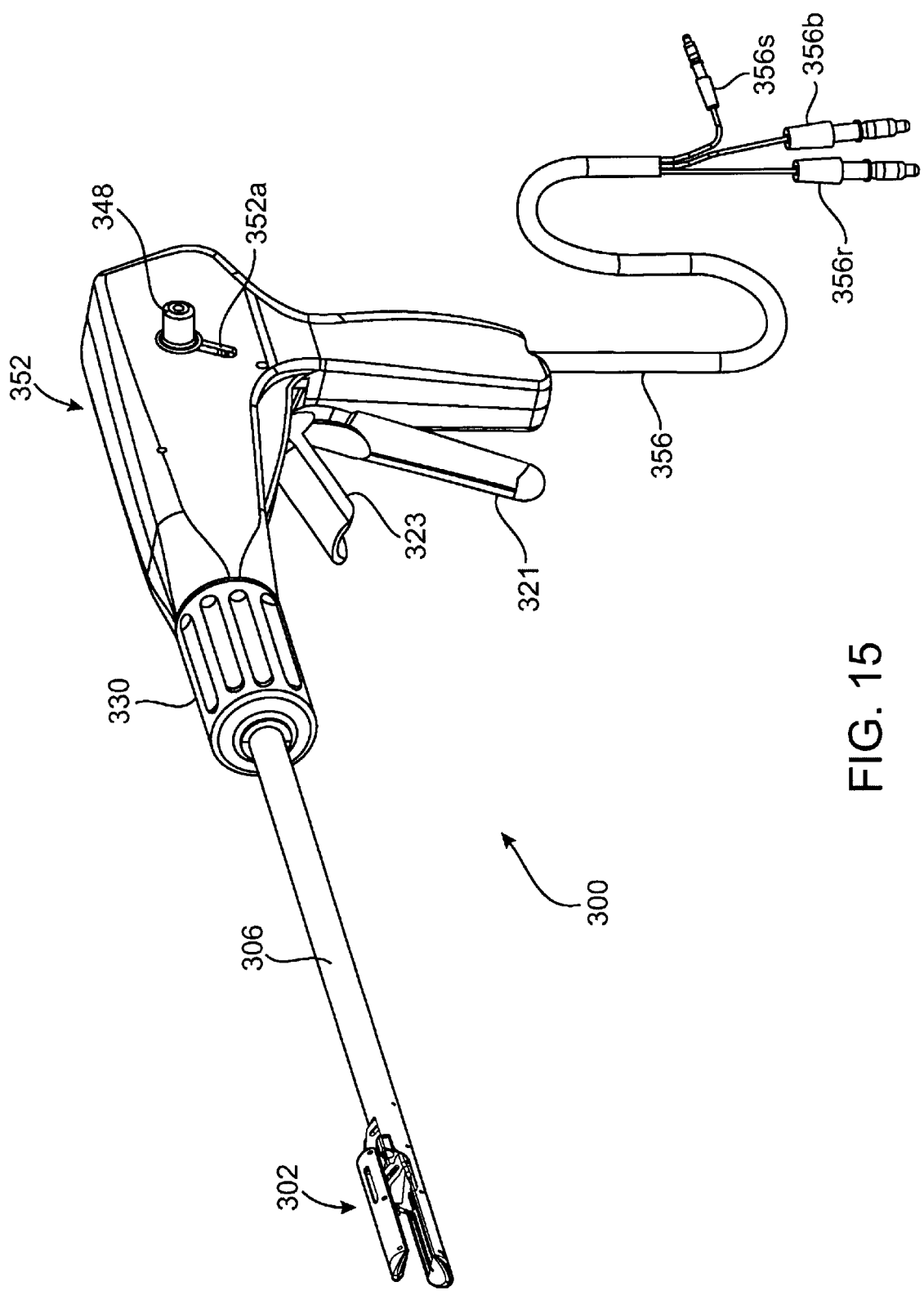
FIG. 15 illustrates an exemplary bipolar surgical instrument constructed in accordance with the principals of the present invention.
Figure 16A:
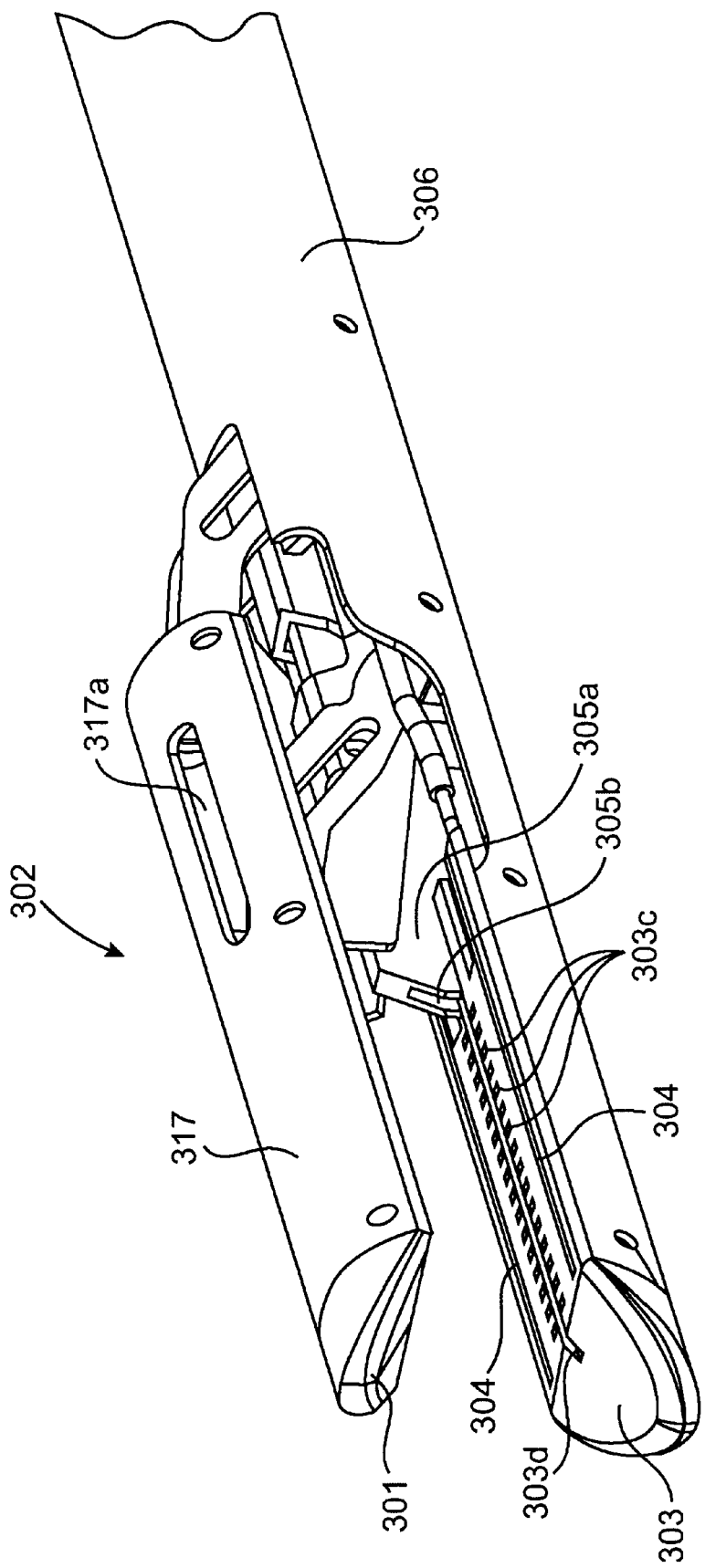
FIGS. 16A illustrates an isolated top to bottom view of a pair of actuable jaws of FIG. 15.
Figure 16B:
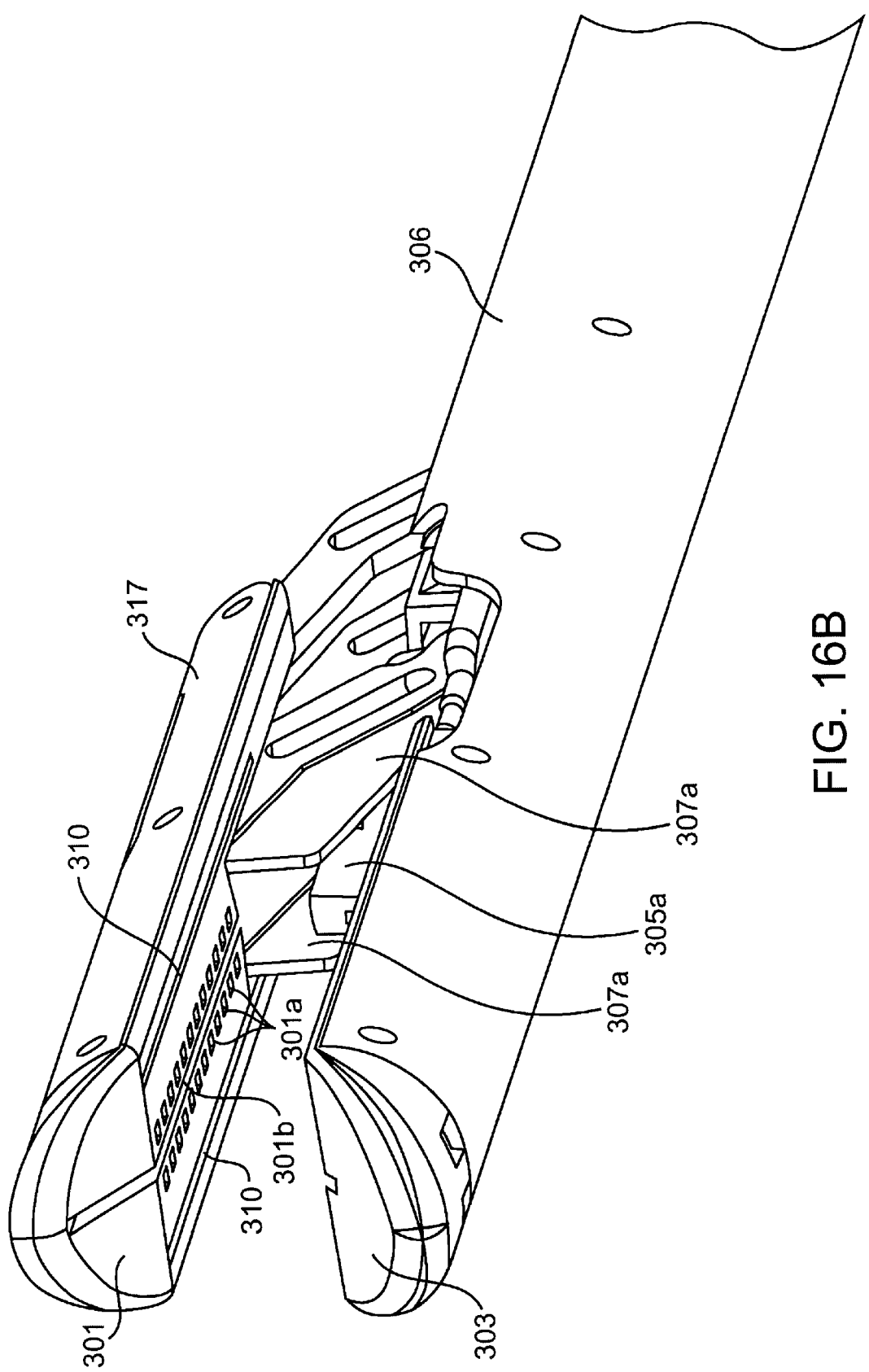
FIG. 16B illustrates an isolated bottom to top view of the pair of actuable jaws of FIG. 15.
Figure 17:
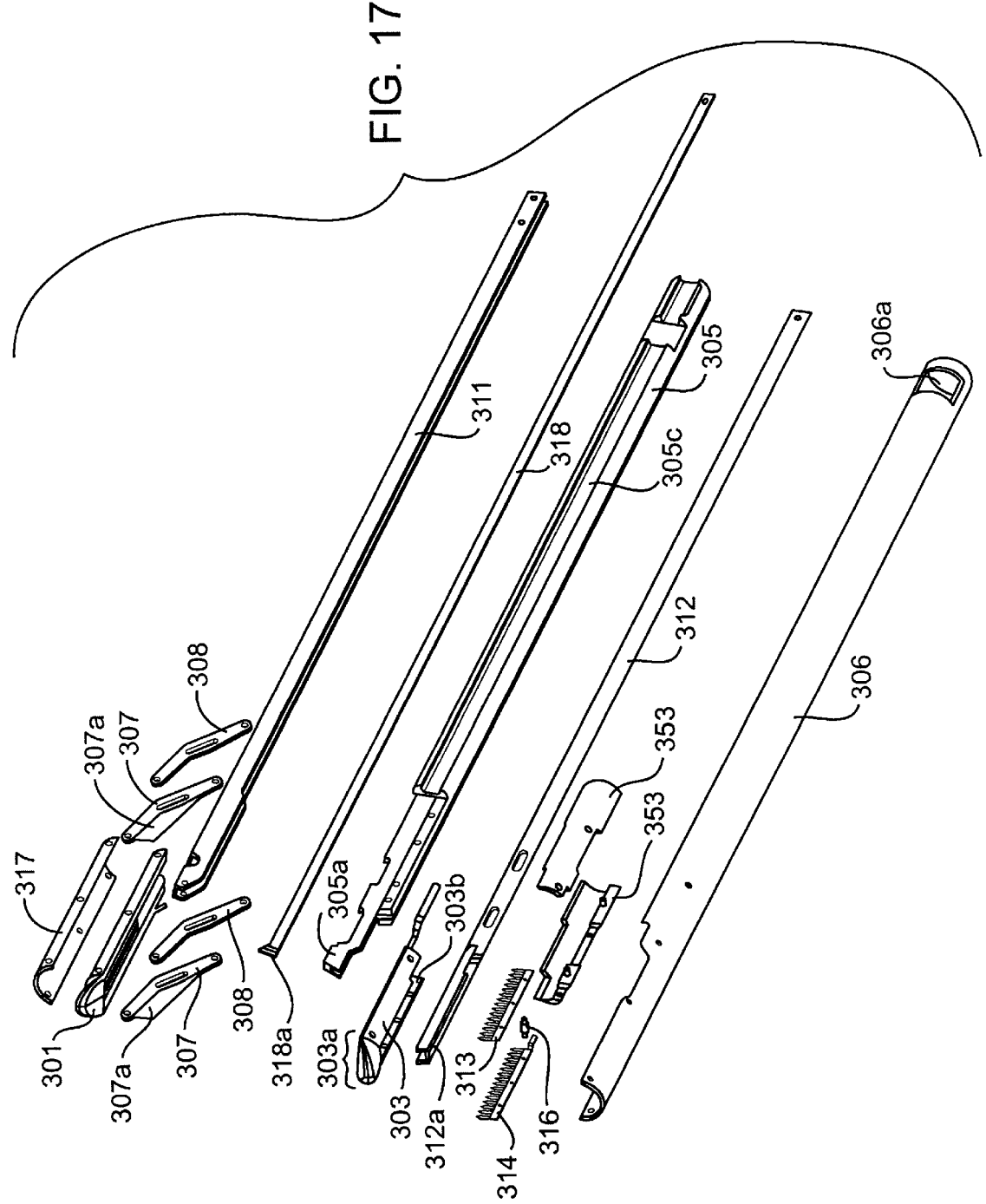
FIG. 17 illustrated an exploded view of the pair of actuable jaws of FIG. 15.
Figure 18A:
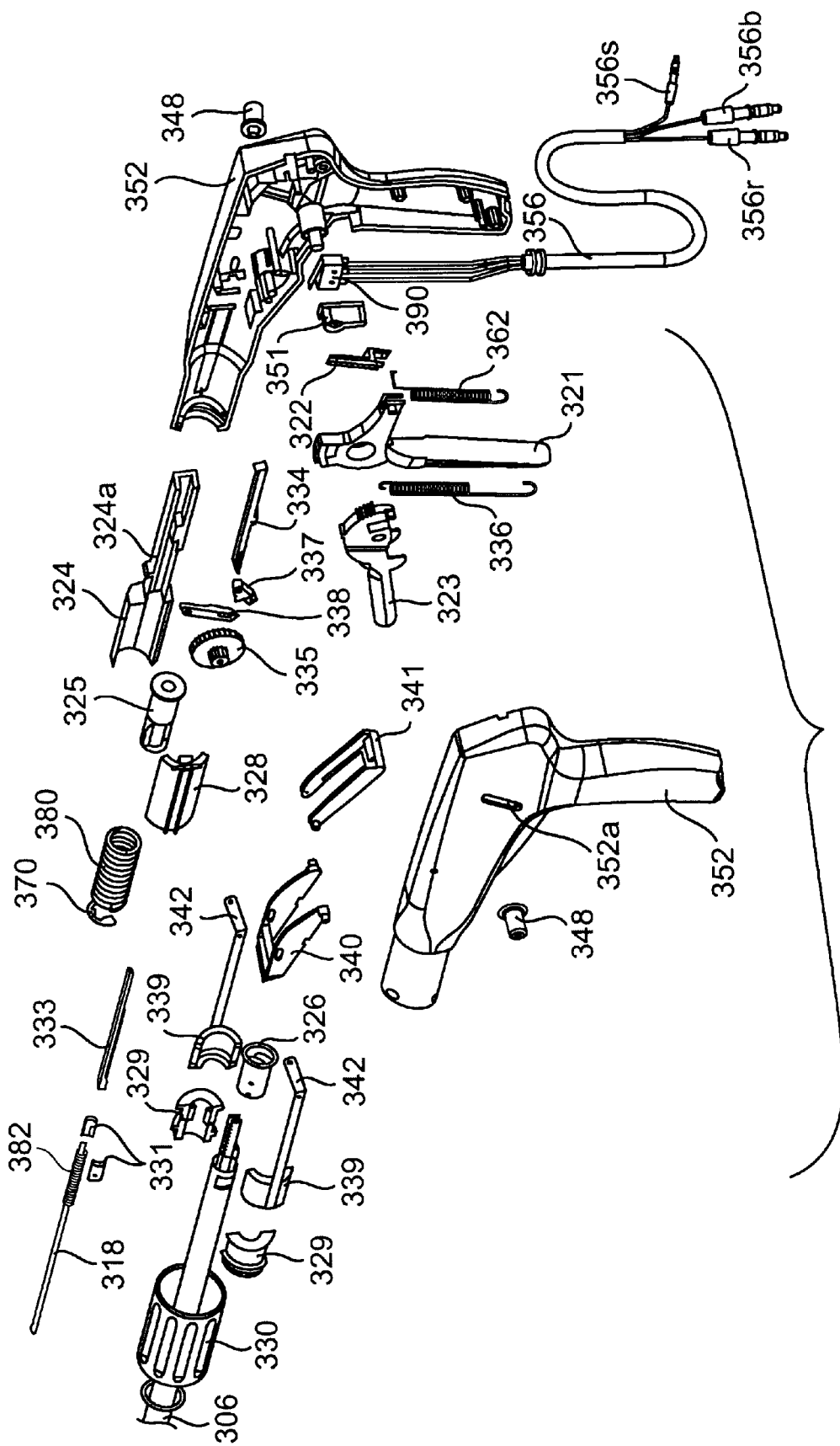
FIG. 18A illustrates an exploded view of a handle of the device of FIG. 15.
Figure 18B:
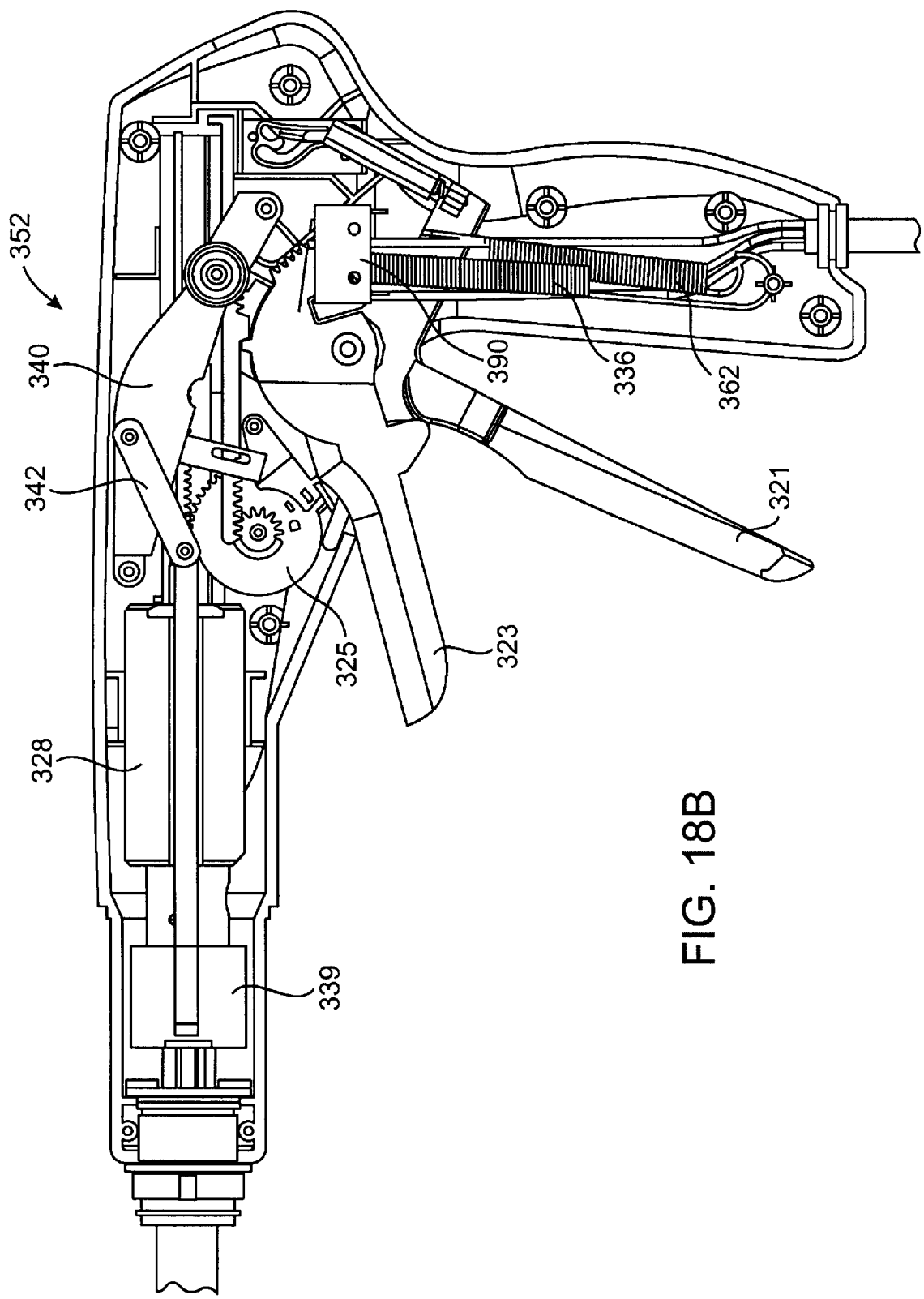
FIG. 18B illustrates a cross sectional view of the handle of the device of FIG. 15.
Figure 19:
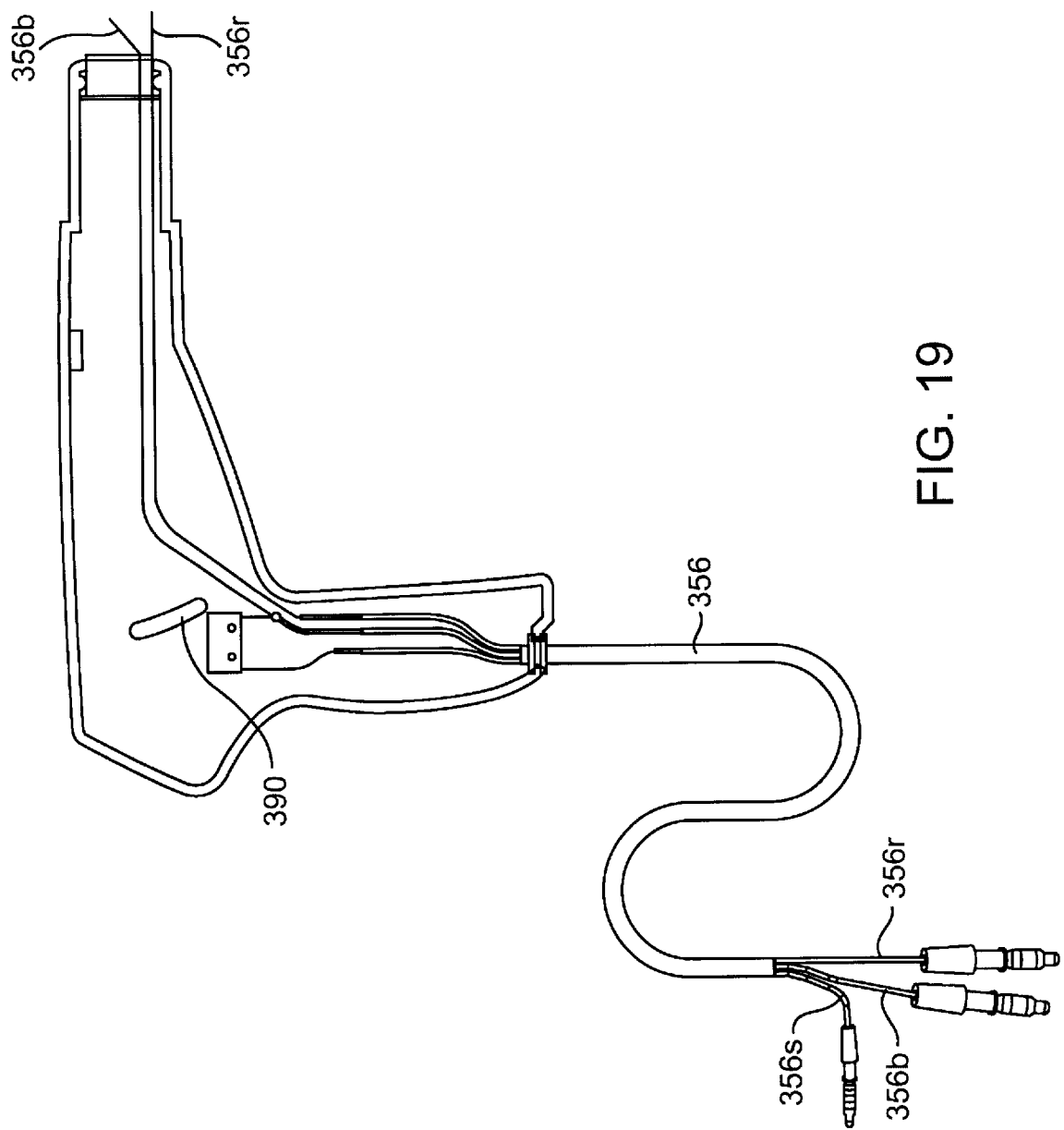
FIG. 19 illustrates the electrical connections of the device of FIG. 15.

Referring now to FIGS. 15, 16A–16F, 17, 18A, 18B, 19, 20A–20D, an exemplary bipolar surgical instrument 300 having a pair of opposed jaws 302, a handle 352, and a shaft 306 therebetween, is illustrated. The pair of opposed jaws 302 include an arrangement of surface electrodes 304 and 310, as shown in FIGS. 16A and 16B respectively, and lines 313 and 314 of tissue-penetrating electrodes, as shown in FIG. 16D. Lines 313 and 314 of tissue-penetrating electrodes are mounted by an electrically conductive spacer 316 in a cavity 303b of an electrically insulating lower jaw 303 (FIG. 17). The tissue-penetrating elements 313 and 314 are free to reciprocate within the cavity 303b and are connected to a lifer 312 that may be actuated by knobs 348 on the handle 352. The knobs 348 are movable along slots 352a which causes link toggles 340 and 341 to move an intermediate link 342, as best seen in FIG. 18A. These links move a lifter coupler 339 forward or backward which in turn advances or retracts the lifter 312. Inclined slots 312a in a distal end of the lifter 312 cause tissue-penetrating electrodes 313 and 314 to reciprocate between a retracted or lowered configuration (FIG. 16C) and an advanced or raised configuration (FIG. 16D). An interlock 324a on a drive cage 324 prevents the link toggle 340 and thereby the knobs 348 from moving until the jaws 302 have been clamped. As described above, clamping the tissue beforehand protects the tissue-penetrating electrodes 313 and 314, i.e., from bending, and facilitates proper alignment of the tissue-penetrating electrodes 313 and 314 into the tissue. Once the jaws 302 have been clamped and the tissue-penetrating elements 313 and 314 advanced via downward advancement of the knob 348 along slot 352a, a micro switch 390 may be activated by depression of the lowered knob 348. The micro switch 390 connects a signal wire 356s with a black wire 356b, which in turn begins the energy application cycle, as depicted in FIG. 19. The signal wire 356s, the black wire 356b, and a red wire 356r may be partially covered by a sheath 356.

Figure 16C:
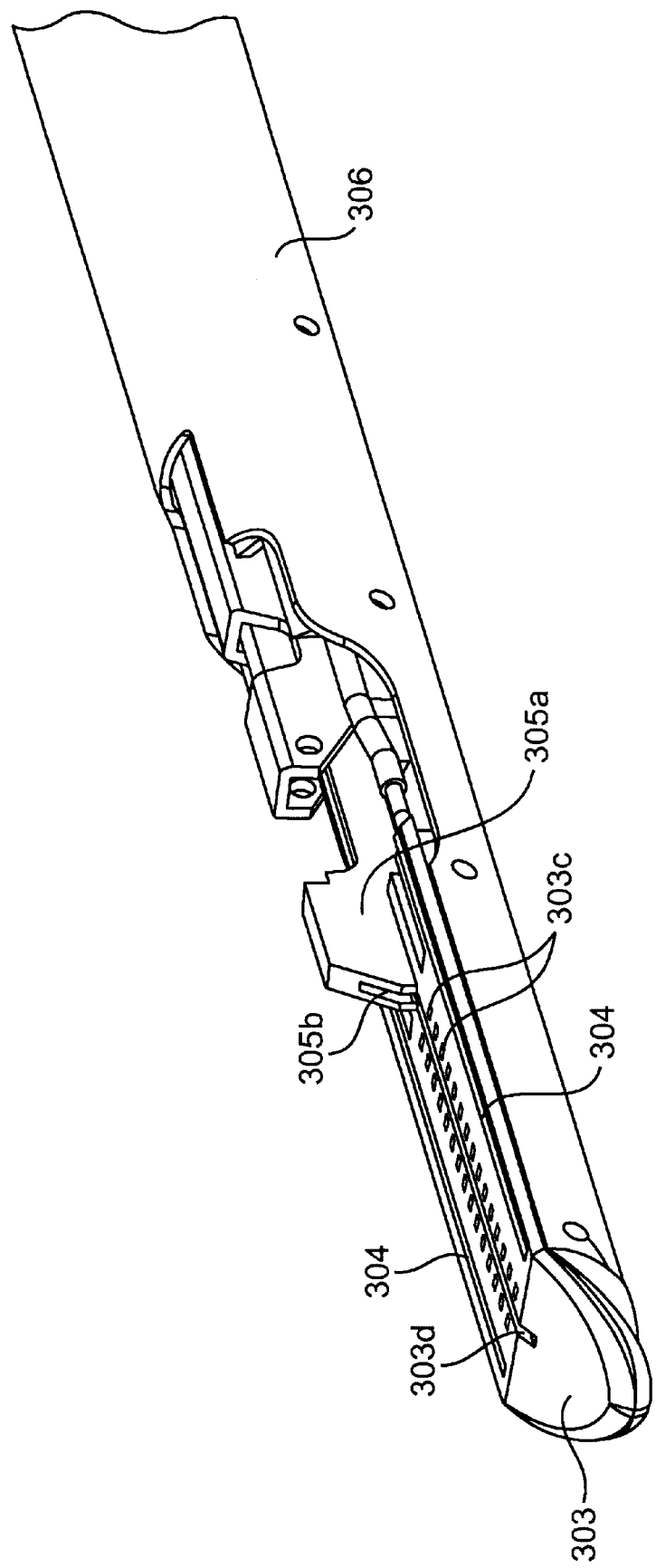
FIG. 16C illustrates an isolated view of an exposed lower jaw of FIG. 15.
Figure 16D:
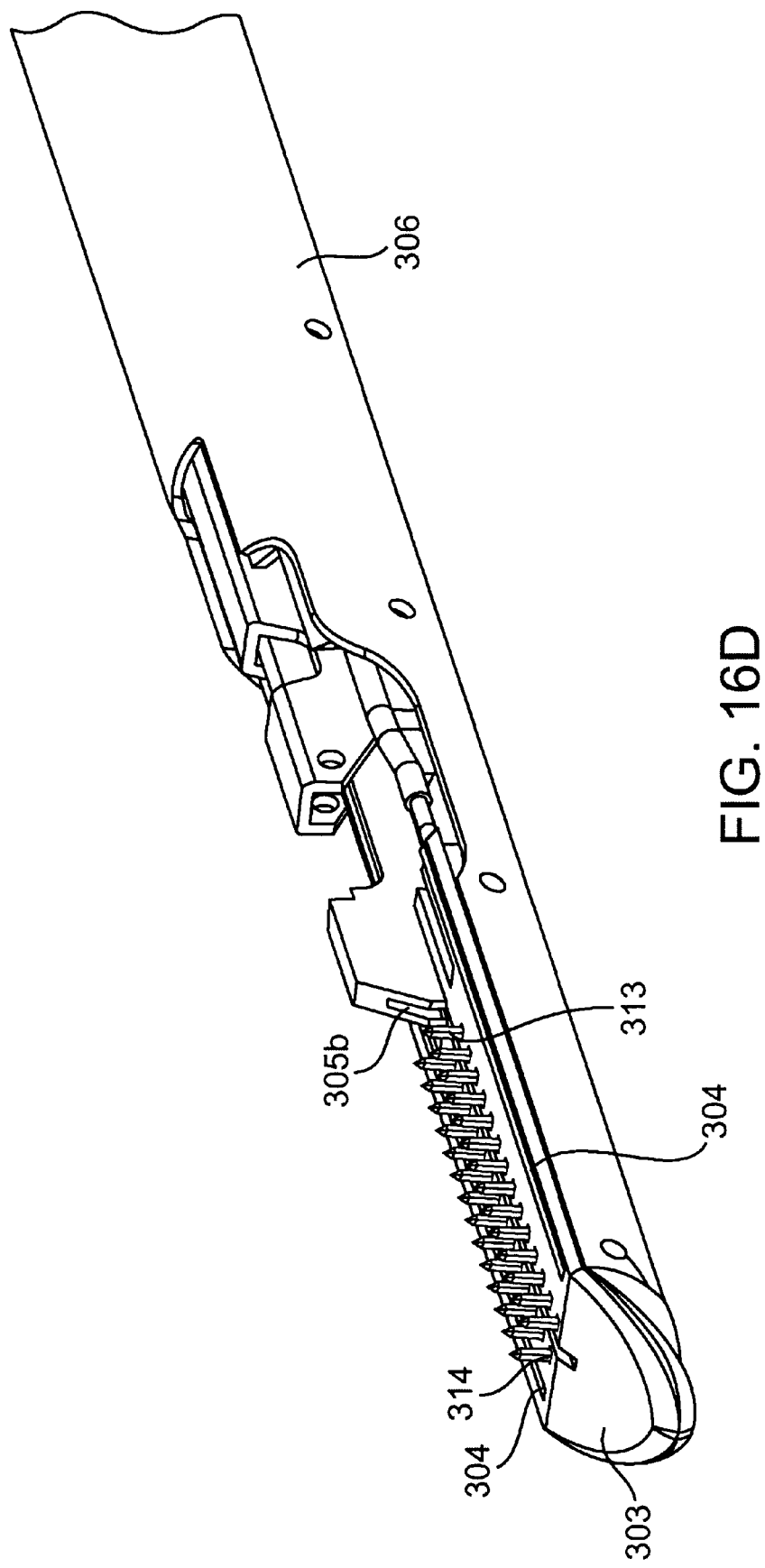
FIG. 16D illustrates an isolated view of an exposed lower jaw of FIG. 15 with two lines of tissue-penetrating elements in an advanced configuration.

The elongate surface electrodes 304 are mounted in the electrically insulating lower jaw 303 which is mounted inside the shaft 306, as shown in FIG. 16C. The lower jaw 303 has a radius 303a along its outside edge to minimize unnecessary tissue trauma. Additionally, the lower jaw 303 has a plurality of holes 303c along the lines 313 and 314, and spaced inwardly from the elongate surface electrodes 304. A channel 303d may be formed along a center line of the lower jaw 303 for receiving a cutting blade 318a. A tissue stop 305a may additionally be formed at an end of a main guide 305 to prevent loading of tissue beyond the tissue-penetrating elements 313 and 314 and to ensure that the cutting blade 318a is protected when it is filly retracted. The main guide 305 may have a channel 305c to provide clearance for the wires 356b and 356r to run to the surface electrodes 304 and 310 and the tissue-penetrating electrodes 313 and 314. The main guide 305 may also have a slot 305b to receive the cutting blade 318a and cover plates 353.

The jaws 302 have a lower jaw structure formed from the shaft 306 and the lower jaw 303, as described above, and an upper jaw structure formed from an upper jaw 301 with a four bar linkage. The upper jaw structure includes a sheath 317 surrounding the molded upper jaw 301, wherein the upper jaw 301 and sheath 317 may have a perforation 317a, channel, outlet, slot, opening, or the like to permit release of steam during use. A bottom view of the upper jaw 301 is best illustrated in FIG. 16B. The upper jaw 301 includes a pair of surface electrodes 310, a relief channel 301b for receiving the cutting blade 318a, and relief holes 301a for receiving upper tips of the tissue-penetrating electrodes 313 and 314 when they are in a completely advanced position.

The upper jaw 301 is actuated by a mechanism made up of links 307 and 308 (FIG. 17). The links 307 and 308 are sized such that a clamping force is preferentially biased toward a tip of the device to help maintain parallelism and minimize tip deflection. Links 307 may have tissue stops 307a to further ensure that tissue is not loaded beyond the tissue-penetrating elements 313 and 314. The links 307 and 308 are actuated by a pusher 311 which in turn is controlled by a drive bushing 326 (FIG. 18A). The bushing 326 is actuated by the drive cage 324 which contains a constrained spring 380 within the cage cover 328. The constrained spring 380 via clip 370 constrains a driving spool 325 so as to limit a force that can be applied to the pusher 311. This in turn limits a grasping force applied to the tissue by the upper jaw 301 so that only a sufficient force to clamp the tissue is applied. The drive cage 324 is connected to a clamp trigger 321 which is clamped by a user and unclamped by a spring 362 (FIGS. 18A and 18B). The clamp trigger 321 has a means of latching and unlatching without secondary operation by the user by the use of a latch link 322 riding in a complex groove in a latch bracket 351. In this way, the jaws 302 can be moved between an open configuration (FIG. 20A) and a closed configuration (FIG. 20B).

A Rotational grip 330 is attached between the proximal end of the shaft 306 and the handle 352. The rotational grip allows for the shaft 306 and the jaws 302 to be rotated relative to the handle 352, up to about 90° in a clockwise and/or counter-clockwise direction. This facilitates loading and clamping of the tissue by the jaws 302 and further minimizes or prevents any tissue deflection when the jaws 302 are closed. Cover plates 329 engage a vertical groove 306a on the shaft 306 to ensure that the handle 352 is secured to the shaft 306.

Figure 16F:
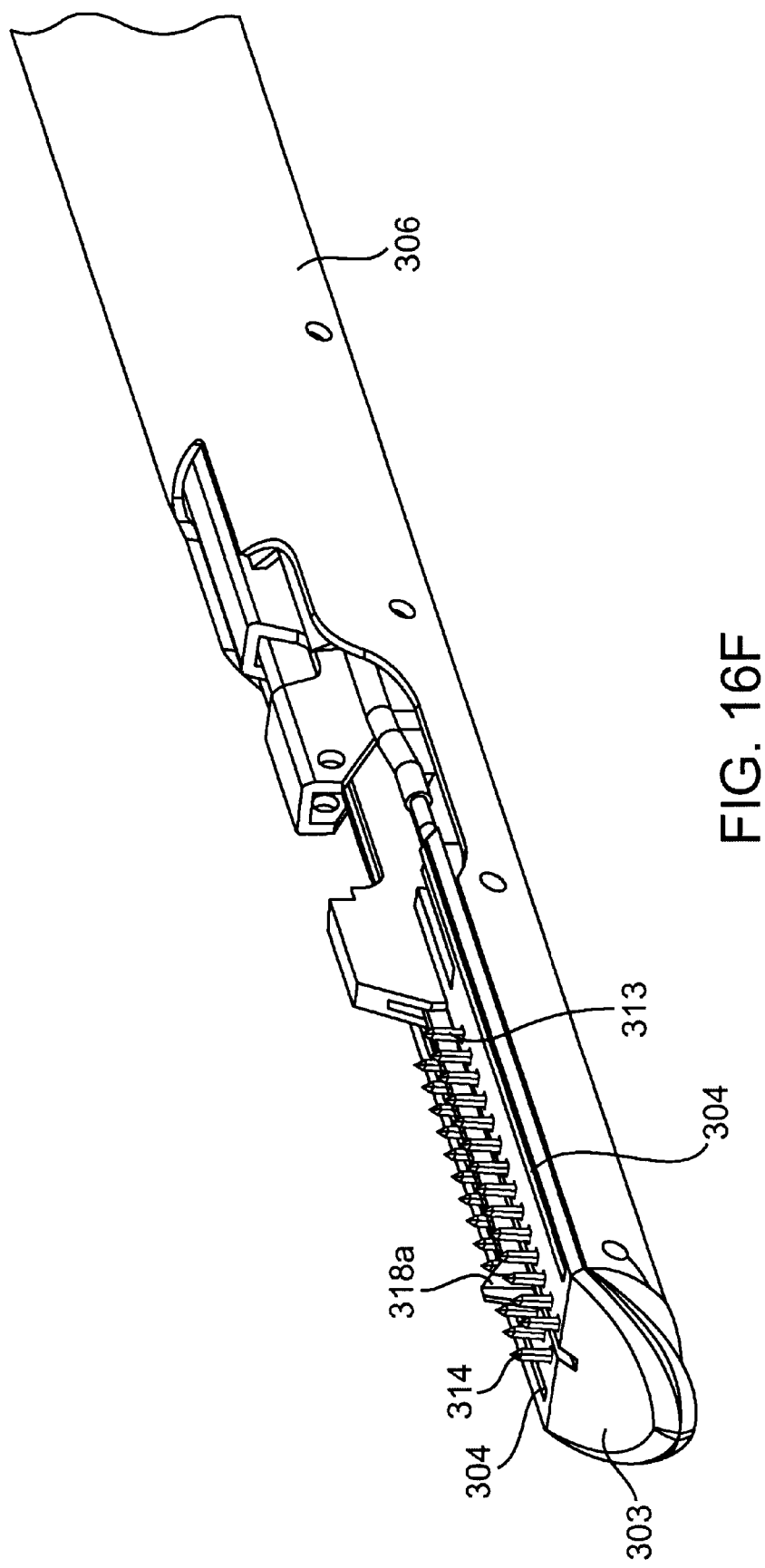
FIG. 16F illustrates an isolated view of an exposed lower jaw of FIG. 15 carrying two lines of tissue-penetrating elements and a cutting blade.

The cutting blade 318a is formed at a forward end of an elongate blade structure 318, as shown in FIGS. 16E and 16F. The elongate blade structure 318 having a spring 382 at its is proximal end is coupleable to a secondary cutting rack 333 via a coupler 331 (FIG. 18A). The cutting rack 333 is driven by a spur gear 335 which in turn is driven by a primary cutting rack 334. The primary cutting rack 334 is driven by a blade trigger 323 which is returned by a spring 336. Interlock links 337 and 338 ensure that the tissue-penetrating elements 313 and 314 are actuated prior to actuation of the cutting blade 318a. In this way, the tissue-penetrating elements 313 and 314 can facilitate proper alignment of the tissue during cutting. The elongate blade structure 318 is received in a slot 305b in the main guide 305, as well as in channel 303d of the lower jaw 303 and channel 301b of the upper jaw 301. Thus, the blade can be advanced (FIGS. 16E and 16F) and retracted (FIG. 16A) by axially moving the blade trigger 323. The cutting blade 318a is disposed in channels 303d and 301b so that it will pass and cut through the tissue which has been previously desiccated by applying high frequency energy through the electrode structures 304, 310, 313, and 314.

Figure 20A:
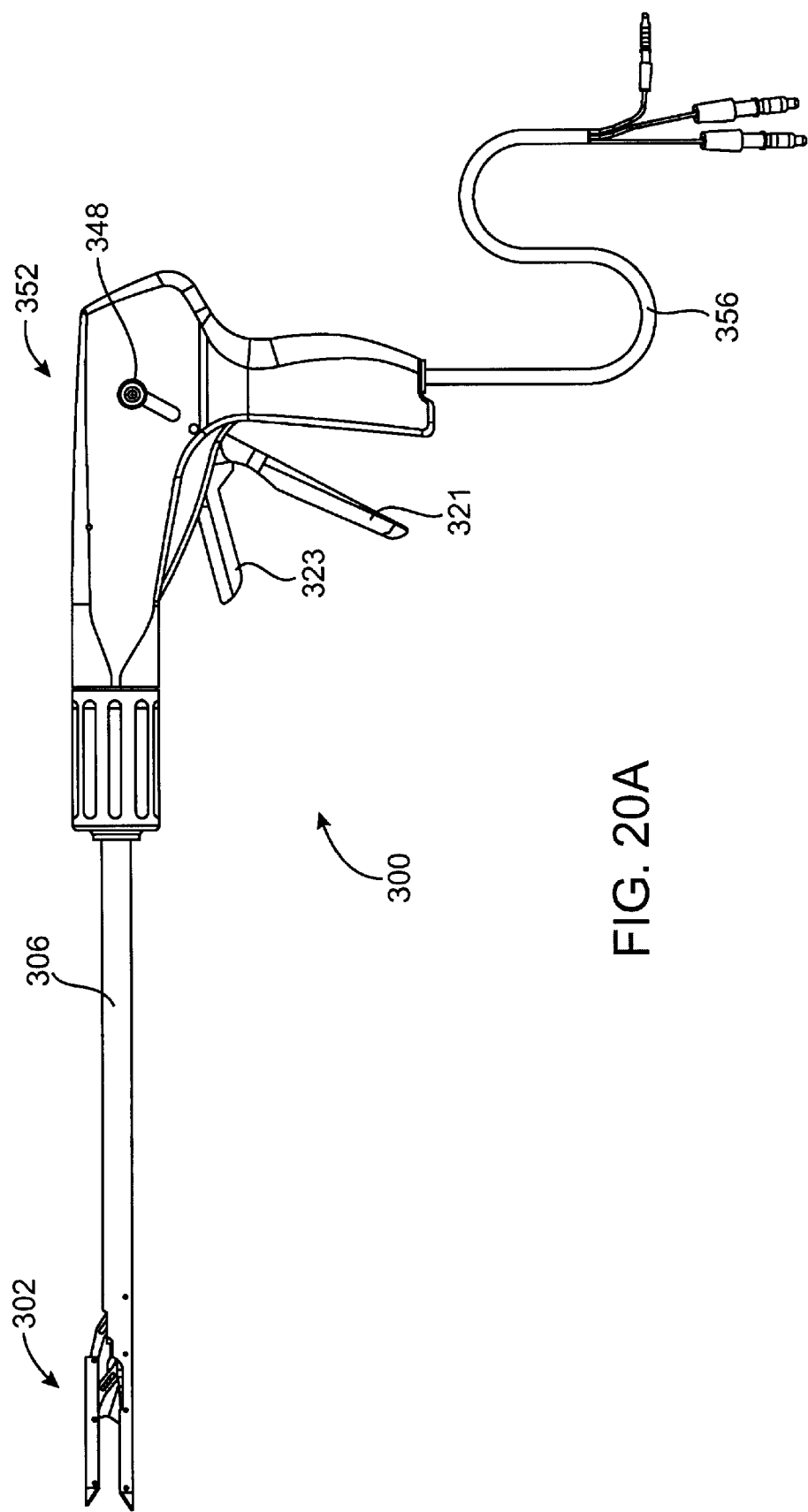
FIGS. 20A–20D illustrate the use of the device of FIG. 15.
Figure 20B:
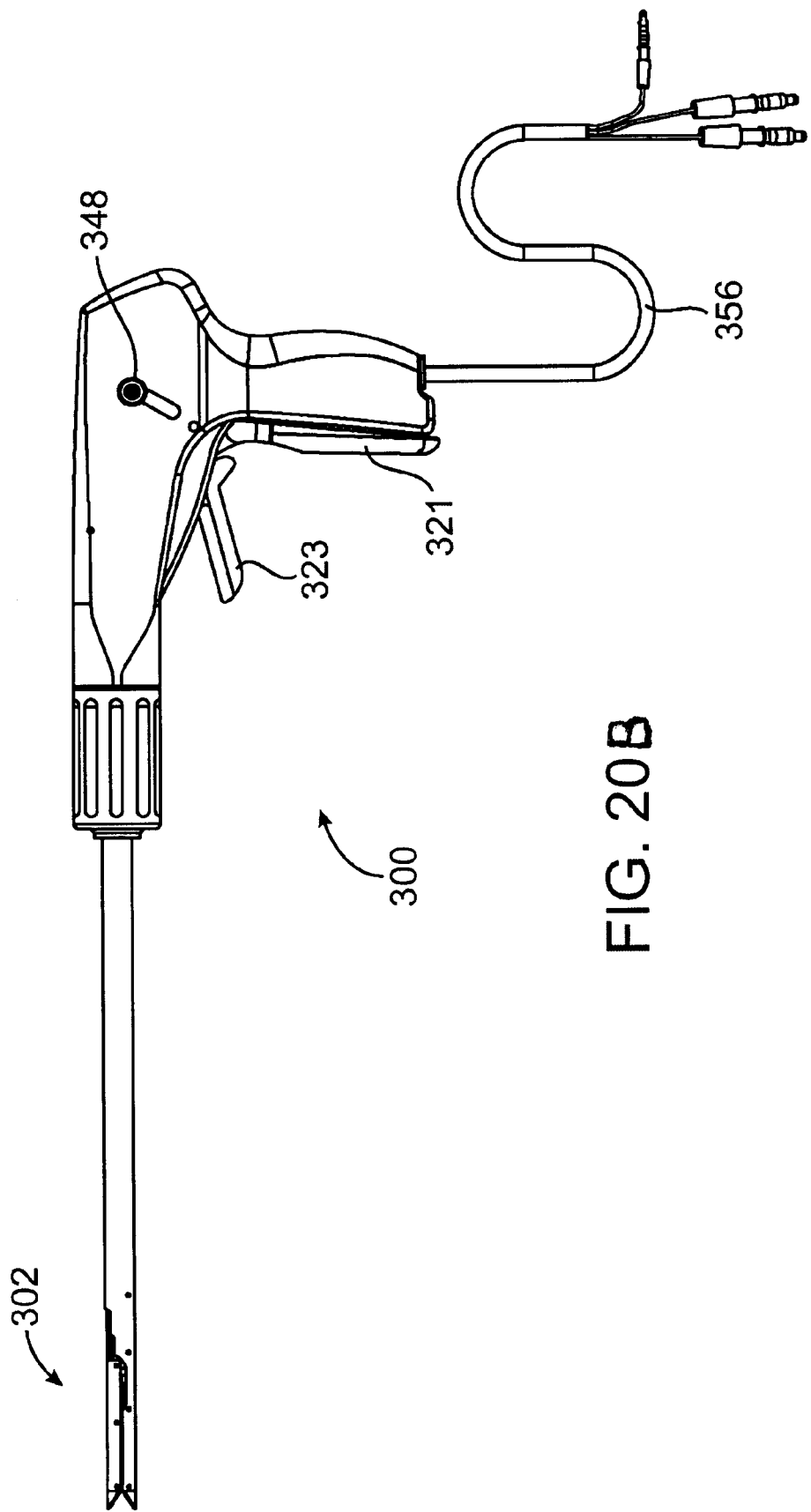
Figure 20C:
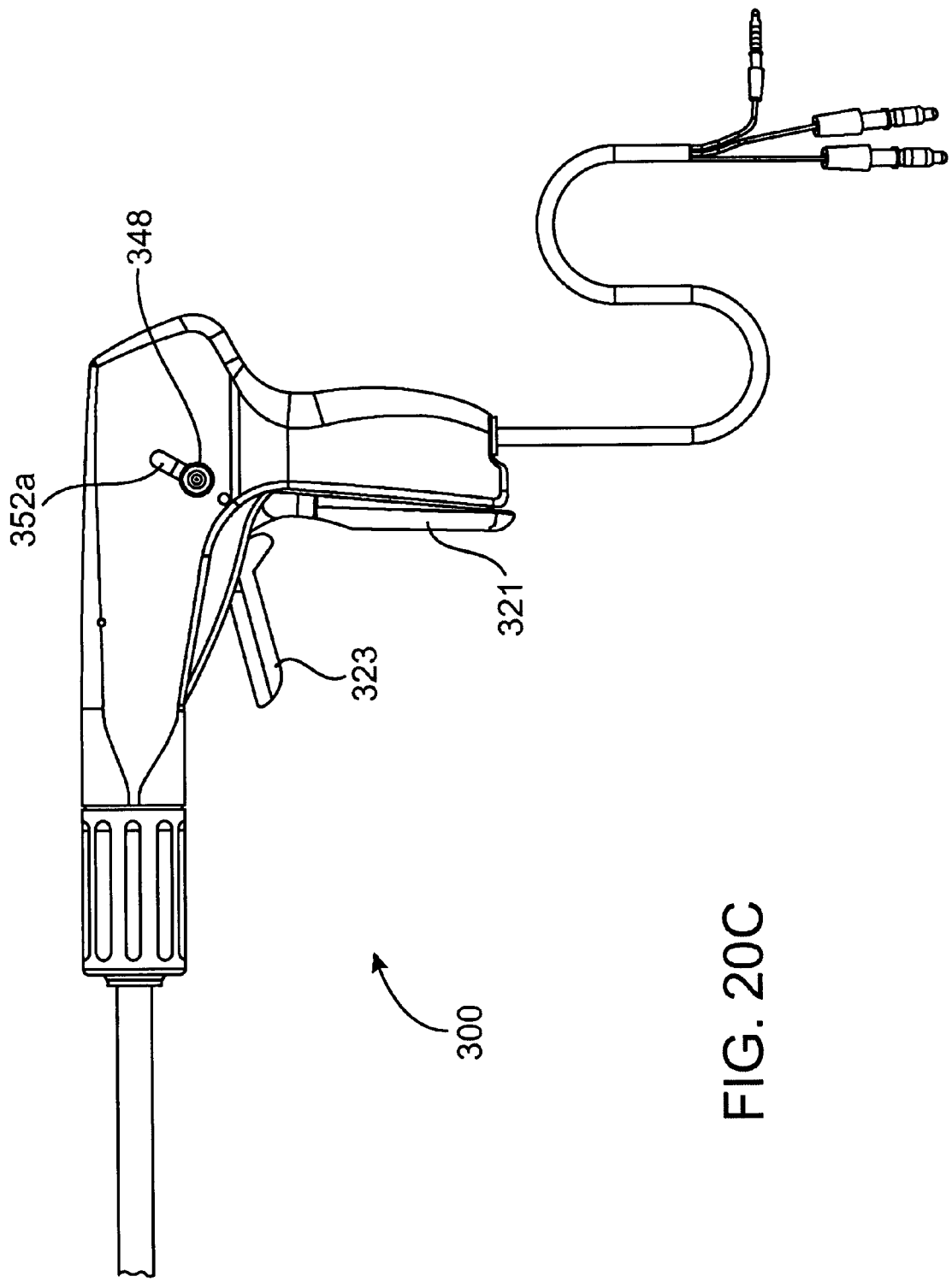
Figure 20D:
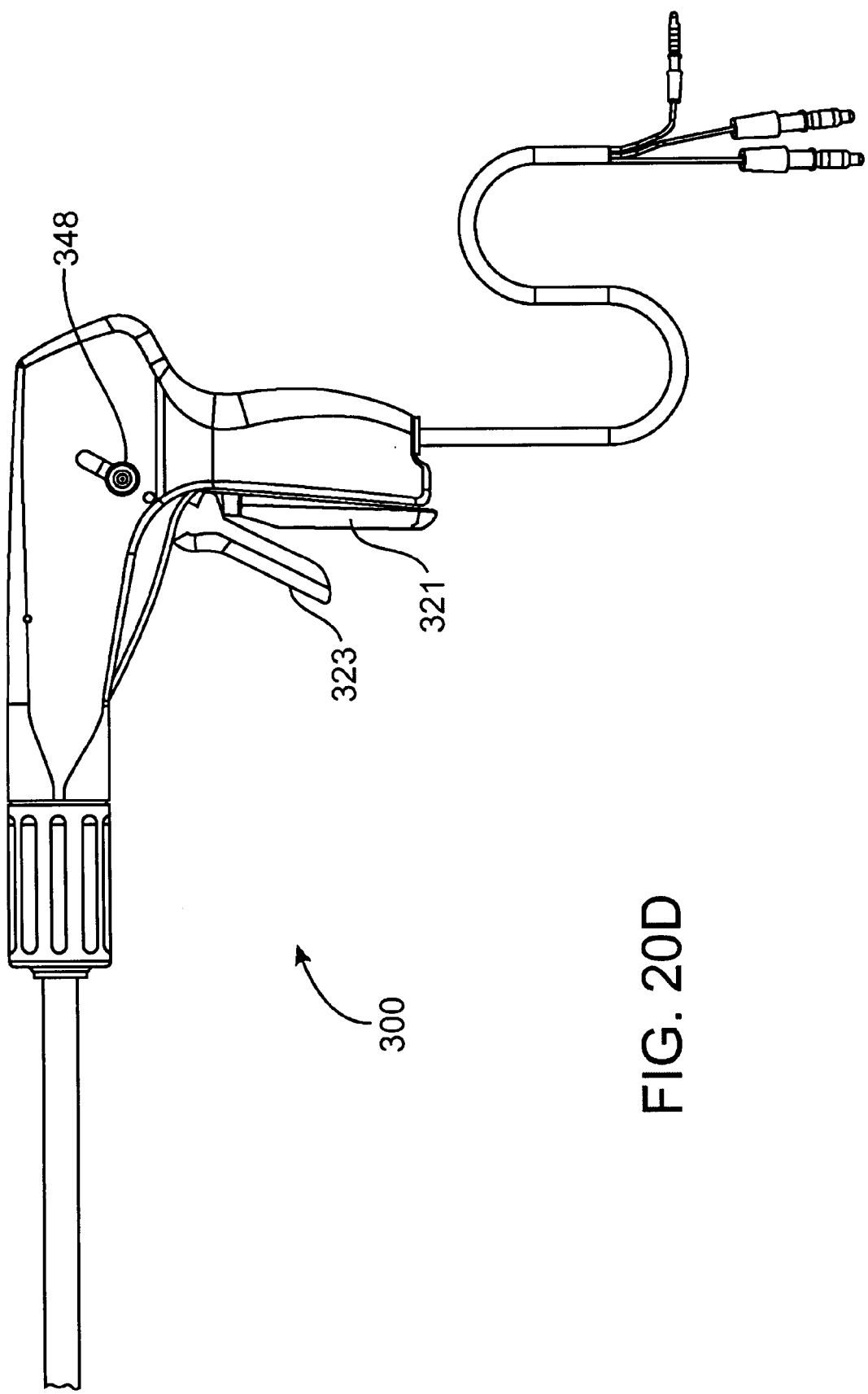

Referring now to FIGS. 20A–20D, operation of the device of FIG. 15 will be described. The jaws 302 will initially be open and the tissue penetrating electrodes 313 and 314 will be retracted into the lower jaw 303, as shown in FIG. 20A. After positioning a target tissue structure between the jaws 302, the jaws can be closed capturing the tissue by full actuation of the clamp trigger 321, as shown in FIG. 20B. The tissue-penetrating elements are then advanced relative to the lower jaw 303 by advancing the knob 348 downward along slot 352a, as shown in FIG. 20C, causing the electrodes 313 and 314 to penetrate the tissue. Radiofrequency or other high frequency energy will then be applied to the tissue by depression of the knob 348. The tissue may be fully desiccated with all the advantages of the use of tissue-penetrating electrodes as described above. After adequate desiccation is achieved, the blade 318a can be advanced to cut thought the parallel segments of desiccated tissue by pulling down on the cutting trigger 323, as shown in FIG. 20D.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A bipolar surgical instrument comprising:
    a shaft having a proximal end and a distal end;
    a pair of opposed jaws at the distal end of the shaft;
    a first electrode member comprising a first line of tissue-penetrating elements on one of the jaws;
    a second electrode member comprising a second line of tissue-penetrating elements on one of the jaws, wherein the first and second electrode members are electrically isolated and laterally spaced-apart from each other; and
    a linkage attaching at least one of the jaws to the shaft, wherein the linkage maintains opposed surfaces of the jaws in a generally parallel orientation as the jaws are moved between an opened and closed configuration by the linkage.

2. A bipolar surgical instrument as in claim 1, wherein the linkage is a parallelogram movement linkage.

3. A bipolar surgical instrument as in claim 1, wherein the linkage is a four-bar linkage.

4. A bipolar surgical instrument as in claim 1, wherein the linkage is actuatable by a clamp trigger on a handle attached to the proximal end of the shaft.

5. A bipolar surgical instrument as in claim 1, wherein the lines of tissue-penetrating elements are advanceable and retractable relative to a surface of the jaw upon which they are mounted by a knob on a handle attached to the proximal end of the shaft.

6. A bipolar surgical instrument as in claim 1, further comprising a cutting blade on one of the jaws.

7. A bipolar surgical instrument as in claim 6, wherein the cutting blade is actuatable to cut along a line between the first and second lines of tissue-penetrating elements by a cutting trigger on a handle attached to the proximal end of the shaft.

8. A bipolar surgical instrument as in claim 1, further comprising a rotational grip attached between the proximal end of the shaft and a handle so as to allow rotation of the shaft and jaws relative to the handle.

9. A bipolar surgical instrument as in claim 8, wherein the shaft and jaws are rotatable up to about 90° in a clockwise and/or counter-clockwise direction.

10. A bipolar surgical instrument as in claim 1, further comprising at least one tissue stop attached to one of the jaws.

11. A bipolar surgical instrument as in claim 1, wherein at least one of the jaws is perforated to permit release of steam during use.

12. A bipolar surgical instrument as in claim 1, wherein the electrode members are laterally spaced-apart by a distance in the range from 0.5 mm to 10 mm.

13. A bipolar surgical instrument as in claim 1, wherein the electrode members have a length in the range from 1 mm to 50 mm.

14. A bipolar surgical instrument as in claim 1, wherein electrode members are on the same jaw.

15. A bipolar surgical instrument as in claim 1, wherein the lines of tissue-penetrating elements project toward the opposed jaw.

16. A bipolar surgical instrument as in claim 1, wherein the lines of tissue-penetrating elements lie parallel to each other.

17. A bipolar surgical instrument as in claim 1, wherein the first electrode member is on one jaw and the second electrode member is on the other jaw.

18. A bipolar surgical instrument as in claim 1, wherein the tissue-penetrating elements have a length in the range from 1 mm to 10 mm and a diameter in the range from 0.1 mm to 2 mm.

19. A bipolar surgical instrument as in claim 1, wherein the first and second electrode members each comprise from 3 to 50 tissue-penetrating elements.

20. A method for applying high frequency electrical energy to tissue, said method comprising:

grasping tissue between a first jaw and a second jaw, wherein opposed surfaces of the jaws are maintained in a generally parallel orientation;

advancing a first line of tissue-penetrating elements on one of the jaws and second line of tissue-penetrating elements on one of the jaws through a surface of the jaw upon which they are mounted and into the tissue after grasping the tissue between the jaws, wherein the lines of tissue-penetrating elements are parallel to and laterally spaced-apart from each other;

applying high frequency energy between the first and second lines of tissue-penetrating elements after advancing the lines of tissue-penetrating elements into the tissue.

21. A method as in claim 20, wherein the high frequency energy is applied at a level and for a time sufficient to desiccate substantially all tissue between the electrode members without causing substantial damage to other tissue.

22. A method as in claim 21, wherein the high frequency energy has a frequency from 100 kHz to 2 MHz, a power level from 5 W to 150 W, and is applied for a time less than 5 minutes.

23. A method as in claim 22, further comprising increasing the power level at a predetermined rate from 1 W/sec to 100 W/sec.

24. A method as in claim 23, further comprising terminating the high frequency energy when an impedance of the tissue is in the range from 50 ohms to 1000 ohms.

25. A method as in claim 21, further comprising cutting the tissue along a line between the first and second lines of tissue-penetrating elements after the tissue has been substantially desiccated, wherein the lines of tissue-penetrating elements remain advanced into the tissue.

26. A method as in claim 20, further comprising rotating the jaws up to about 90° in a clockwise and/or counter-clockwise direction prior to grasping the tissue between the jaws.

27. A method as in claim 20, further comprising limiting a grasping force applied to the tissue by the first and second jaws.

28. A method as in claim 19, further comprising receiving upper tips of the lines of tissue-penetrating elements into relief holes of an opposed jaw.

29. A method as in claim 20, further comprising releasing steam during use from a perforation on at least one of the jaws.

30. A method as in claim 20, further comprising retracting the lines of tissue-penetrating elements from the tissue prior to disengaging the jaws.

* * * * *